(12) United States Patent
Saito et al.

(10) Patent No.: US 8,419,646 B2
(45) Date of Patent: Apr. 16, 2013

(54) BLOOD PRESSURE ESTIMATION APPARATUS AND BLOOD PRESSURE ESTIMATION METHOD

(75) Inventors: Masatoshi Saito, Tokyo (JP); Sakae Omura, Tokyo (JP); Toru Shinzato, Toyohashi (JP)

(73) Assignees: Asahi Kasei Kabushiki Kaisha, Osaka-Shi (JP); Nextier Corporation, Toyohashi-Shi (JP)

(*) Notice: Subject to any disclaimer, the term of this patent is extended or adjusted under 35 U.S.C. 154(b) by 359 days.

(21) Appl. No.: 12/935,741

(22) PCT Filed: Apr. 9, 2009

(86) PCT No.: PCT/JP2009/057250
§ 371 (c)(1), (2), (4) Date: Oct. 21, 2010

(87) PCT Pub. No.: WO2009/125811
PCT Pub. Date: Oct. 15, 2009

(65) Prior Publication Data
US 2011/0125033 A1    May 26, 2011

(30) Foreign Application Priority Data
Apr. 9, 2008 (JP) .................. 2008-101842

(51) Int. Cl.
*A61B 5/02* (2006.01)
(52) U.S. Cl.
USPC ............ 600/485; 600/481; 600/490; 600/528
(58) Field of Classification Search .......... 600/481–499, 600/528, 586
See application file for complete search history.

(56) References Cited

U.S. PATENT DOCUMENTS

| 5,010,889 A * | 4/1991 | Bredesen et al. ............. 600/528 |
| 6,231,523 B1 * | 5/2001 | Tomita .......................... 600/586 |

(Continued)

FOREIGN PATENT DOCUMENTS

| JP | 5-91980 A | 4/1993 |
| JP | 5-115547 A | 5/1993 |

(Continued)

OTHER PUBLICATIONS

International Search Report PCT/JP2009/057250 dated Jul. 7, 2009.

(Continued)

*Primary Examiner* — Patricia Mallari
*Assistant Examiner* — Tiffany Weston
(74) *Attorney, Agent, or Firm* — Birch, Stewart, Kolasch & Birch, LLP

(57) ABSTRACT

To provide a non-invasive blood pressure estimation apparatus, which can accurately estimate systolic blood pressure from blood flow sound of a dialysis patient and continuously estimate systolic blood pressure by continuously picking up the blood flow sound. A blood pressure estimation apparatus creates a standard pulse curve by relating a start point and end point of a rising phase of a pulse wave to diastolic blood pressure and systolic blood pressure, respectively, creates a correspondence curve between blood flow sound power and estimated blood pressure by contrasting the standard pulse curve with the blood flow sound power curve obtained from blood flow sound at a shut site, with the two curves plotted on the same time axis, derives a systolic blood pressure estimation linear function from the correspondence curve, inputs a measured maximum value of the blood flow sound power into the linear function, and thereby estimates systolic blood pressure.

16 Claims, 45 Drawing Sheets

U.S. PATENT DOCUMENTS

| | | | |
|---|---|---|---|
| 2004/0249293 A1* | 12/2004 | Sandler et al. | 600/481 |
| 2005/0010118 A1 | 1/2005 | Toyoda et al. | |
| 2005/0283087 A1 | 12/2005 | Takazawa et al. | |

FOREIGN PATENT DOCUMENTS

| | | |
|---|---|---|
| JP | 10-52490 A | 2/1998 |
| JP | 3083378 B2 | 9/2000 |
| JP | 2005-27800 A | 2/2005 |
| JP | 2006-176 A | 1/2006 |
| JP | 2006-247193 A | 9/2006 |

OTHER PUBLICATIONS

English translation of International Preliminary Report on Patentability mailed Dec. 9, 2010, in PCT International Application No. PCT/JP2009/057250.

* cited by examiner

Time

Time

Time [min.]

Maximum value of blood flow sound power

Maximum value of blood flow sound power

Maximum value of blood flow sound power

Maximum value of blood flow sound power

BLOOD PRESSURE ESTIMATION APPARATUS AND BLOOD PRESSURE ESTIMATION METHOD

TECHNICAL FIELD

The present invention relates to an apparatus and method which non-invasively estimate blood pressure values of a subject such as a dialysis patient by measuring blood flow sounds of the subject.

BACKGROUND ART

For example, blood pressure often falls suddenly during dialysis. For early detection of such an event, it is necessary to measure blood pressure on a frequent basis, and ideally on a continuous basis during dialysis. The most common method involves measuring blood pressure intermittently, but frequently, with a manchette of a sphygmomanometer kept attached. However, this method has problems. Namely, measurements can be taken at intervals of 15 minutes at best even if taken frequently. At a higher frequency, the patient would feel uncomfortable and congestion would occur downstream of the manchette. Also, the manchette has to be wrapped around the upper limb opposite a shunt side, causing the patient to feel uncomfortable with both upper limbs bound.

In this way, since the patient feels uncomfortable with both upper limbs bound if blood pressure is measured from the upper limb on the side opposite the shunt side, it is advisable to measure blood pressure continuously from the upper limb on the shunt side. As a method for measuring blood pressure continuously from the arm on the shunt side during dialysis, Patent Literature 1 describes a method for estimating blood pressure using a shunt blood flow velocity measured with an infrared Doppler meter. The method estimates blood pressure using a relationship (proportionality relationship), measured in advance, between shunt blood flow velocity and blood pressure. With this method, it is necessary to ensure that an infrared beam will hit the center of a flow line of shunt blood flow. This is extremely difficult under circumstances in which the patient will move the arm even slightly. Also, the equipment is expensive. Patent Literatures 2 and 3 disclose methods for estimating blood flow condition at a site of shunt creation by monitoring vibrations and blood flow sounds at the site of shunt creation during dialysis. However, these methods measure a blood flow volume rather than blood pressure. Patent Literature 4 discloses means for measuring pressure in the blood flowing through a shunt blood vessel used during dialysis, identifying and isolating vibrations produced by pumps and the like of a dialysis monitoring system, and thereby measuring a pulse rate and blood pressure values. However, the technique has drawbacks: pressure of drawn blood is low even on the arterial side, it is difficult to isolate noise produced by equipment, there is a possibility that dialyzed blood may flow backward, and so on. Also, the technique has a problem in measurement accuracy.

CITATION LIST

Patent Literature

Patent Literature 1: Japanese Patent Laid-Open No. 2006-247193
Patent Literature 2: Japanese Patent Laid-Open No. 10-52490
Patent Literature 3: Japanese Patent No. 3083378
Patent Literature 4: Japanese Patent Laid-Open No. 2005-27800

SUMMARY OF INVENTION

Technical Problem

In view of the problems with the conventional techniques described above, an object of the present invention is to provide a non-invasive blood pressure estimation apparatus and blood pressure estimation method which can accurately estimate systolic blood pressure from blood flow sounds of a subject such as a dialysis patient and can continuously estimate systolic blood pressure by continuously picking up the blood flow sounds of the subject.

Solution to Problem

After conducting active studies to solve the above problems, the present inventors have completed the present invention based on a finding that systolic blood pressure can be accurately estimated from a correspondence curve between blood flow sound power and estimated blood pressure. The correspondence curve is created as follows: a standard pulse curve is created relating a start point and end point of a rising phase of a pulse wave to diastolic blood pressure and systolic blood pressure, respectively, by capitalizing on the fact that differences among individuals are insignificant in the rising phase of pulse waves, the standard pulse curve is contrasted with a blood flow sound power curve obtained from blood flow sound of a subject and plotted on the same time axis as the standard pulse curve, and thus the correspondence curve is created.

Specifically, the present invention relates to:

(1) A blood pressure estimation apparatus which estimates blood pressure of a subject using a standardization mode and an estimation mode, comprising: blood flow sound power waveform calculation means for determining a blood flow sound power waveform from blood flow sound of the subject in the standardization mode; blood pressure measuring means for measuring reference systolic blood pressure and reference diastolic blood pressure of the subject in the standardization mode; standard pulse curve storing means for storing a standard pulse curve whose time axis and pulse pressure axis have been standardized such that times and pulse pressures at a start point and an end point of a rising phase of a pulse wave measured in advance will be constant, in the standardization mode; first computing means for determining a correspondence curve which represents a relationship between blood flow sound power and estimated blood pressure from relationships among the blood flow sound power waveform, the reference systolic blood pressure, the reference diastolic blood pressure, and the standard pulse curve, in the standardization mode; blood flow sound power measuring means for continuously measuring the blood flow sound of the subject and the blood flow sound power in the estimation mode; and second computing means for continuously estimating blood pressure from the blood flow sound power measured continuously, using the correspondence curve in the estimation mode.

(2) The blood pressure estimation apparatus according to (1), wherein the first computing means comprises: third computing means for creating a reference blood pressure curve which represents a relationship of blood pressure values to standardized time based on the standard pulse curve by bringing the reference diastolic blood pressure value and the reference systolic blood pressure value measured by the blood pressure measuring means into correspondence with a minimum value and a maximum value of standardized pulse pressure values of the standard pulse curve, respectively; fourth computing means for standardizing a time axis in a rising phase of the blood flow sound power waveform at the time corresponding to the time of measurement of the reference diastolic blood pressure value and the reference systolic blood pressure value and creating a reference blood flow sound power curve which represents a relationship of the blood flow sound power to the standardized time; and fifth computing means for creating the correspondence curve which represents a relationship between the blood flow sound power and the estimated blood pressure in a period of common standardized time based on a relationship between the reference blood pressure curve and the reference blood flow sound power curve in the period of common standardized time.

(3) The blood pressure estimation apparatus according to (2), wherein: the first computing means comprises sixth computing means for calculating a systolic blood pressure estimation linear function which approximates the correspondence curve by passing through a point on the correspondence curve corresponding to an end point of the standardized time; and the second computing means inputs a maximum value of the blood flow sound power measured by the blood flow sound power measuring means into the systolic blood pressure estimation linear function and thereby determines estimated systolic blood pressure.

(4) The blood pressure estimation apparatus according to (3), wherein: the sixth computing means calculates a first systolic blood pressure estimation linear function for the subject and a second systolic blood pressure estimation linear function for the subject, where according to the first systolic blood pressure estimation linear function for the subject, the maximum value of the blood flow sound power during blood pressure estimation falls below the maximum value of the blood flow sound power at the time of measurement of the reference diastolic blood pressure value and the reference systolic blood pressure value and according to the second systolic blood pressure estimation linear function for the subject, the maximum value of the blood flow sound power during blood pressure estimation rises above the maximum value of the blood flow sound power at the time of measurement of the reference diastolic blood pressure value and the reference systolic blood pressure value; and the second computing means determines the estimated systolic blood pressure using the first systolic blood pressure estimation linear function or the second systolic blood pressure estimation linear function depending on variations in the maximum value of the blood flow sound power of the subject during blood pressure estimation.

(5) The blood pressure estimation apparatus according to (4), wherein: the sixth computing means calculates another systolic blood pressure estimation linear function for the subject according to which the maximum value of the blood flow sound power falls to or below a predetermined threshold during the blood pressure estimation; and the second computing means determines the estimated systolic blood pressure using the another systolic blood pressure estimation linear function instead of the first systolic blood pressure estimation linear function if the maximum value of the blood flow sound power of the subject during the blood pressure estimation falls to or below the threshold.

(6) The blood pressure estimation apparatus according to (5), wherein when the maximum value of the blood flow sound power is equal to the threshold, the another systolic blood pressure estimation linear function has a point of intersection with the first systolic blood pressure estimation linear function and approximates the correspondence curve in a range in which the maximum value of the blood flow sound power is not above the threshold.

(7) The blood pressure estimation apparatus according to any one of (4) to (6), wherein: the first systolic blood pressure estimation linear function is defined by a line which has a slope joining a point existing between 5/12 and 7/12 (both inclusive) of the standardized time and a point existing between 9/12 and 11/12 (both inclusive) of the standardized time when a start point and the end point of the standardized time on the correspondence curve obtained by the fifth computing means are taken as 0 and 1, respectively; and the second systolic blood pressure estimation linear function is defined by a line which has a slope joining that point on the correspondence curve which corresponds to the end point of the standardized time and a point existing between 9/12 and 11/12 (both inclusive) of the standardized time when the start point and the end point of the standardized time on the correspondence curve obtained by the fifth computing means are taken as 0 and 1, respectively.

(8) The blood pressure estimation apparatus according to any one of (3) to (7), wherein during blood pressure estimation performed by the first computing means, a computational operation for finding the systolic blood pressure estimation linear function is performed a plurality of times to correct the systolic blood pressure estimation linear function.

(9) The blood pressure estimation apparatus according to any one of (1) to (8), further comprising: mode setting means for setting one of the standardization mode and the estimation mode; information input means for inputting data of at least the reference diastolic blood pressure value, the reference systolic blood pressure value, and the standard pulse curve; information output means for outputting at least estimated blood pressure values; and blood pressure value storing means for storing the reference diastolic blood pressure value and the reference systolic blood pressure value.

(10) The blood pressure estimation apparatus according to any one of (1) to (9), wherein the pulse wave used to create the standard pulse curve is an average of a plurality of pulse waves obtained from a plurality of unspecified subjects.

(11) The blood pressure estimation apparatus according to any one of (1) to (10), wherein the pulse wave used to create the standard pulse curve is a pulse wave of the subject whose blood pressure is estimated.

(12) A blood pressure estimation method for estimating blood pressure, comprising a standardization mode and an estimation mode, wherein: the standardization mode comprises: a first step of measuring blood flow sound of a subject and determining a blood flow sound power waveform from the measured blood flow sound, a second step of measuring reference systolic blood pressure and reference diastolic blood pressure of the subject, a third step of preparing a standard pulse curve whose time axis and pulse pressure axis have been standardized such that times and pulse pressures at a start point and an end point of a rising phase of a pulse wave measured in advance will be constant, and a fourth step of determining a correspondence curve which represents a relationship between blood flow sound power and estimated blood pressure from relationships among the blood flow sound power waveform, the reference systolic blood pressure, the reference diastolic blood pressure, and the standard pulse curve in the standardization mode; and the estimation mode comprises: a fifth step of continuously measuring the blood flow sound of the subject and the blood flow sound power, and a sixth step of estimating blood pressure continuously from the blood flow sound power measured continuously, using the correspondence curve in the estimation mode.

(13) The blood pressure estimation method according to (12), wherein the fourth step comprises: a step of creating a reference blood pressure curve which represents a relationship of blood pressure values to standardized time based on the standard pulse curve by bringing the reference diastolic blood pressure value and the reference systolic blood pressure value into correspondence with a minimum value and a maximum value of standardized pulse pressure values of the standard pulse curve, respectively; a step of standardizing a time axis in a rising phase of the blood flow sound power waveform at the time corresponding to the time of measurement of the reference diastolic blood pressure value and the reference systolic blood pressure value and creating a reference blood flow sound power curve which represents a relationship of the blood flow sound power to the standardized time; and a step of creating the correspondence curve which represents a relationship between the blood flow sound power and the estimated blood pressure in a period of common standardized time based on a relationship between the reference blood pressure curve and the reference blood flow sound power curve in the period of common standardized time.

(14) The blood pressure estimation method according to (13), wherein: the fourth step calculates a systolic blood pressure estimation linear function which approximates the correspondence curve by passing through a point on the correspondence curve corresponding to an end point of the standardized time; and the sixth step inputs a maximum value of the blood flow sound power measured by the fifth step into the systolic blood pressure estimation linear function and thereby determines estimated systolic blood pressure.

(15) The blood pressure estimation method according to (14), wherein: the fourth step calculates a first systolic blood pressure estimation linear function for the subject and a second systolic blood pressure estimation linear function for the subject, where according to the first systolic blood pressure estimation linear function for the subject, the maximum value of the blood flow sound power during blood pressure estimation falls below the maximum value of the blood flow sound power at the time of measurement of the reference diastolic blood pressure value and the reference systolic blood pressure value and according to the second systolic blood pressure estimation linear function for the subject, the maximum value of the blood flow sound power during blood pressure estimation rises above the maximum value of the blood flow sound power at the time of measurement of the reference diastolic blood pressure value and the reference systolic blood pressure value; and the sixth step determines the estimated systolic blood pressure using the first systolic blood pressure estimation linear function or the second systolic blood pressure estimation linear function depending on variations in the maximum value of the blood flow sound power of the subject during blood pressure estimation.

(16) The blood pressure estimation method according to (15), wherein: the fourth step calculates another systolic blood pressure estimation linear function for the subject according to which the maximum value of the blood flow sound power falls to or below a predetermined threshold during the blood pressure estimation; and the sixth step determines the estimated systolic blood pressure using the another systolic blood pressure estimation linear function instead of the first systolic blood pressure estimation linear function if the maximum value of the blood flow sound power of the subject during the blood pressure estimation falls to or below the threshold.

Advantageous Effects of Invention

The present invention can accurately and continuously estimate systolic blood pressure from blood flow sounds of a subject, enabling early detection of a sudden fall in the blood pressure of a dialysis patient, for example, during dialysis.

DESCRIPTION OF EMBODIMENTS

The blood pressure estimation apparatus according to the present invention will be described below with reference to the drawings by citing an embodiment. However, the present invention is not limited to this. The present invention involves a standardization mode and estimation mode. In the standardization mode, systolic blood pressure estimation linear function is determined to estimate systolic blood pressure from blood flow sound power based on a relationship between blood flow sound power and pulse wave. In the estimation mode, the systolic blood pressure is estimated from a maximum value of the blood flow sound power using the systolic blood pressure estimation linear function. A process of the standardization mode is shown in FIG. 1 while process details of the systolic blood pressure estimation mode are shown in FIG. 2.

Figure 1:
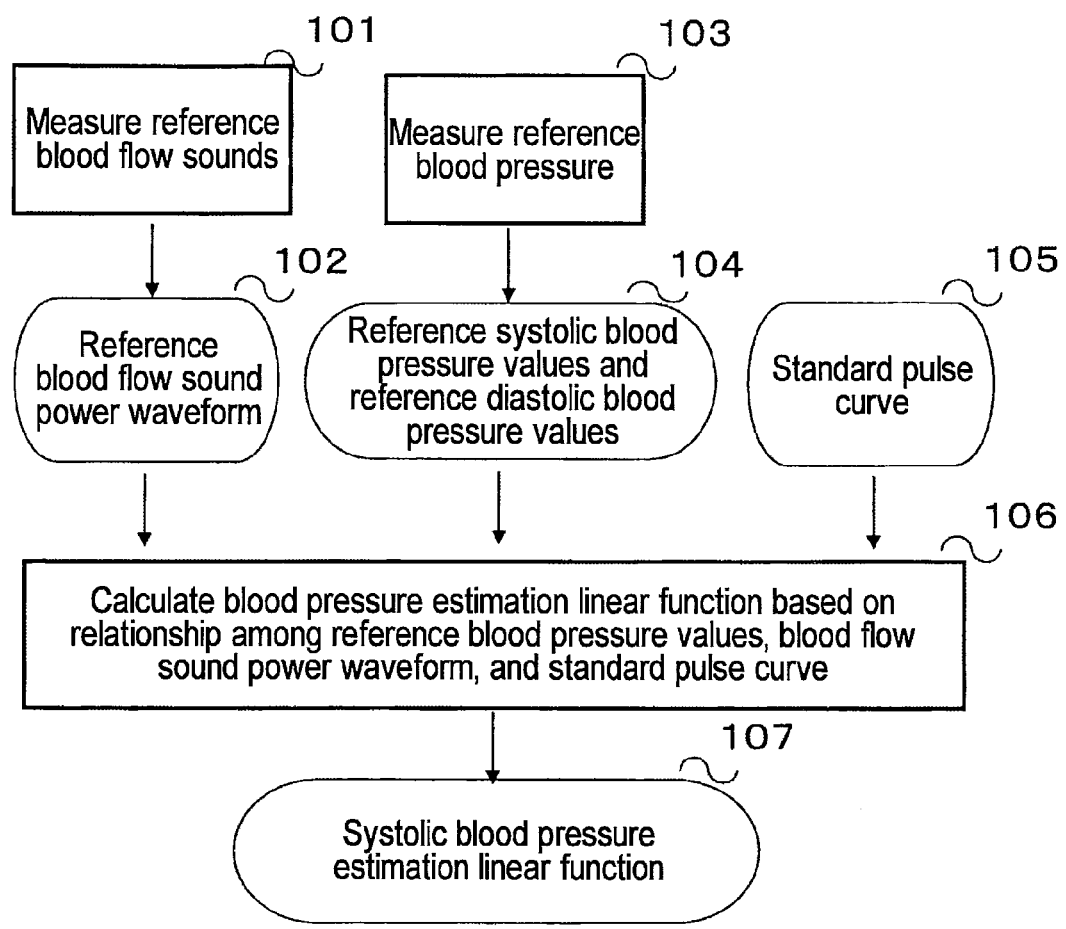
FIG. 1 is a process flow diagram of a standardization mode.

In the standardization mode, as shown in FIG. 1, a reference blood flow sound power waveform 102 is determined first in Step 101 of measuring blood flow sounds for reference. At the same time, systolic blood pressure values and diastolic blood pressure values for reference 104 are determined in Step 103 of measuring blood pressure for reference. Then, a systolic blood pressure estimation linear function 107 is determined in Step 106 of calculating a blood pressure estimation linear function for estimation of systolic blood pressure from a standard pulse curve 105, the reference blood flow sound power waveform 102, and the reference systolic blood pressure values and reference diastolic blood pressure values 104 prepared in advance.

Figure 2:
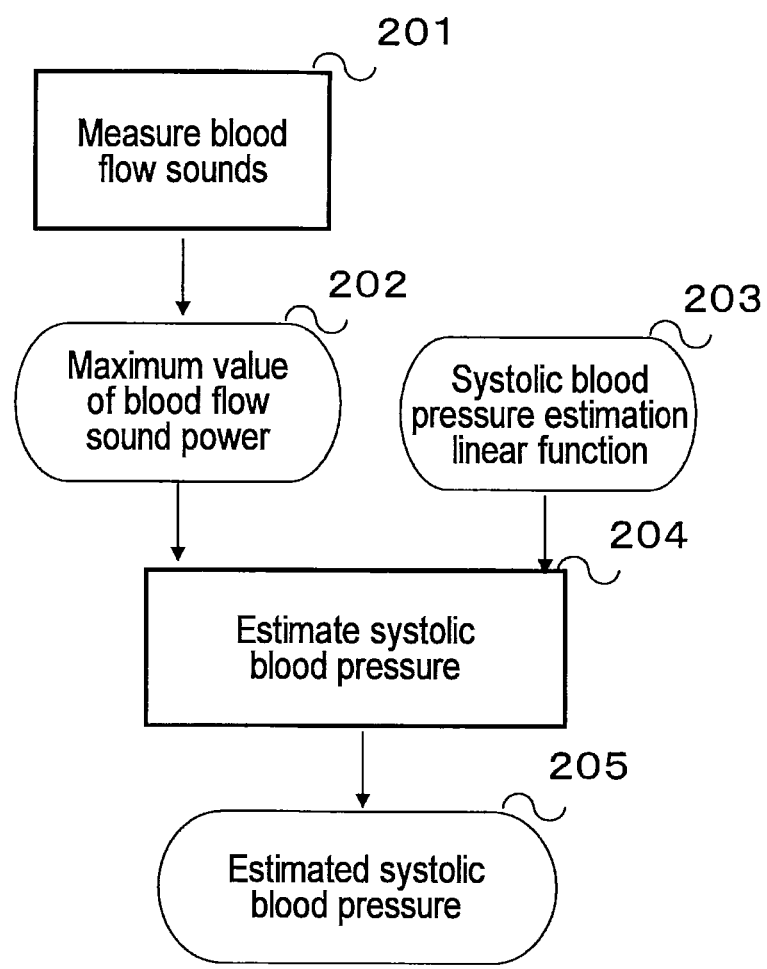
FIG. 2 is a process flow diagram of a systolic blood pressure estimation mode.

In the systolic blood pressure estimation mode, as shown in FIG. 2, a maximum value 202 of the blood flow sound power is determined in Step 201 of measuring blood flow sounds, and then estimated systolic blood pressure 205 is determined in Step 204 of estimating systolic blood pressure from the maximum value 202 of the blood flow sound power using the systolic blood pressure estimation linear function 203 determined in the standardization mode.

Figure 3:
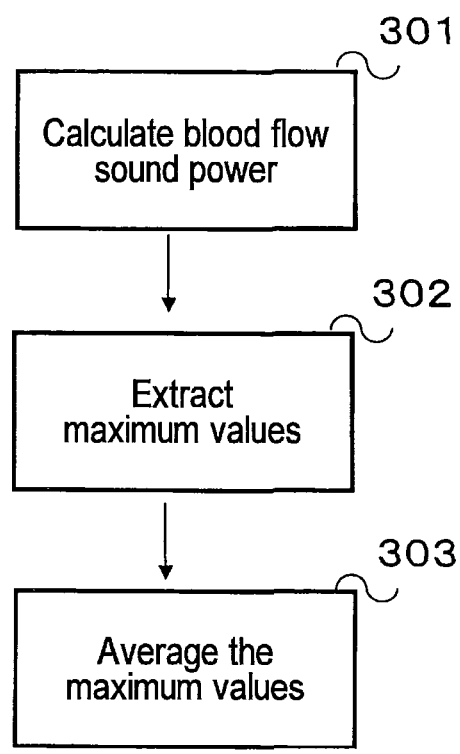
FIG. 3 is a flow diagram of a measurement procedure for blood flow sound power.
Figure 4:
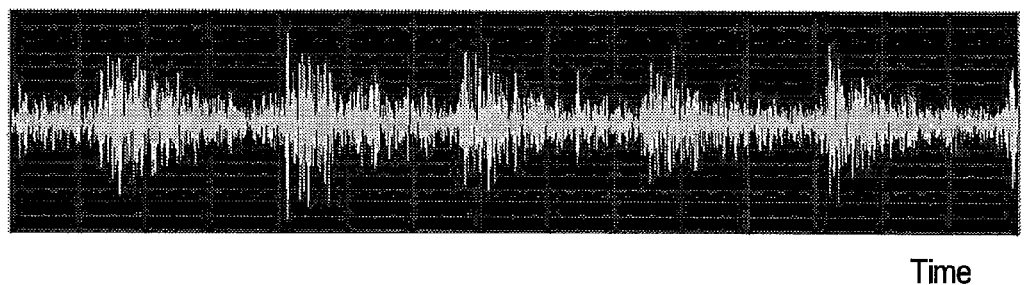
FIG. 4 is a diagram showing an example of blood flow sounds of a subject undergoing dialysis.
Figure 5:
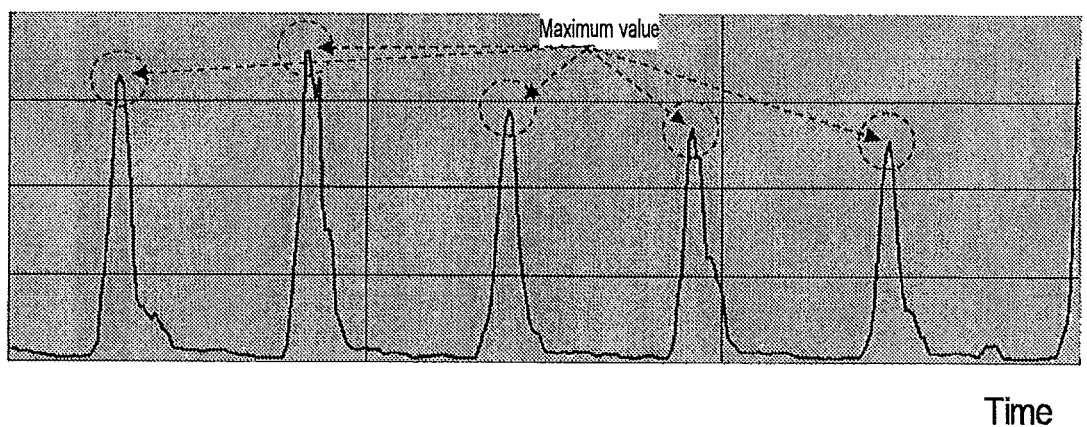
FIG. 5 is a diagram showing an example of blood flow sound power.
Figure 6:
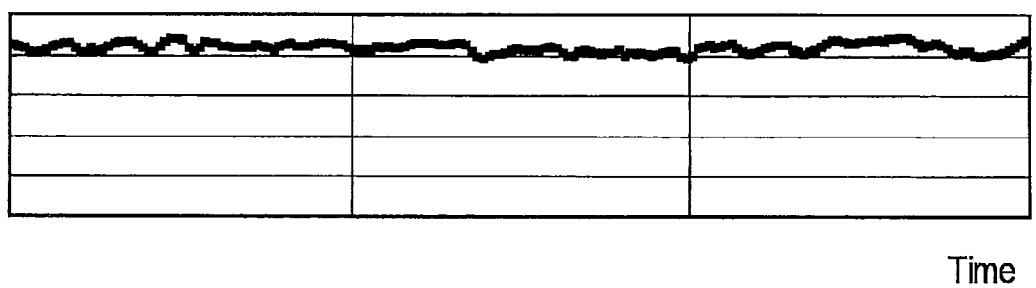
FIG. 6 is a diagram showing an example of average maximum values of blood flow sound power.
Figure 7:
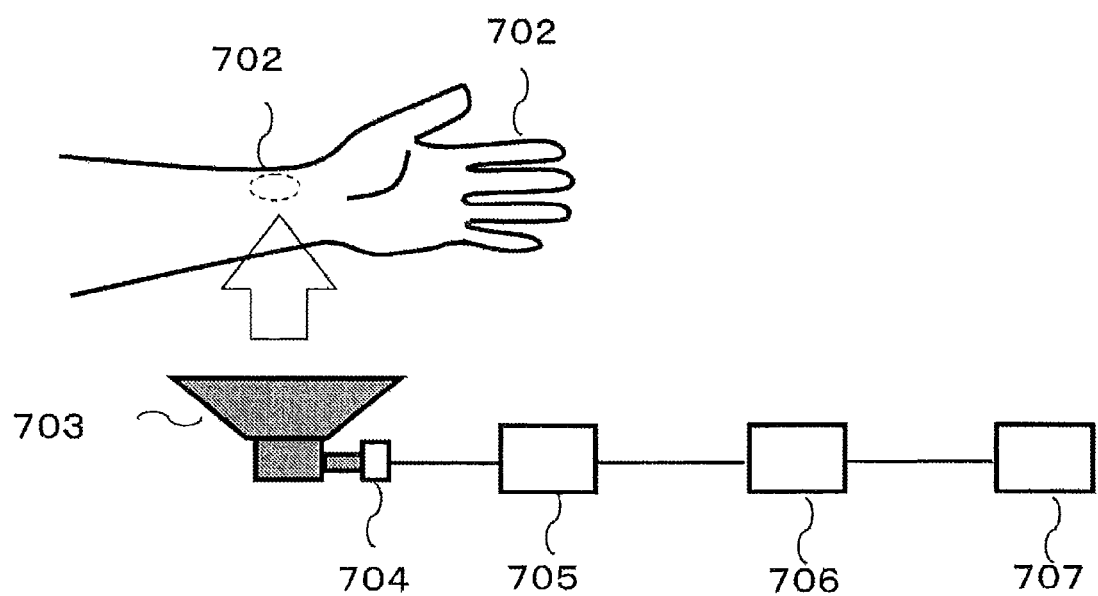
FIG. 7 is a schematic diagram of blood flow sound measuring means.

FIG. 3 is a flow diagram showing details of the process of determining the maximum value 202 of the blood flow sound power in Step 201 of measuring blood flow sounds. FIG. 5 shows examples of outputs from steps when Step 201 is applied to blood flow sounds at a shunt site of a dialysis patient—that is a subject—shown in FIG. 4. First, blood flow sound power is calculated in Step 301 using the blood flow sounds measured in FIG. 4. If a specific frequency band contains noise, the blood flow sounds may be divided into multiple frequency bands and the blood flow sound power may be calculated using blood flow sound signals in frequency bands excluding the specific frequency band. The solid line in FIG. 5 shows blood flow sound power plotted by extracting a frequency band between 0.75 kHz and 1.75 kHz from blood flow sounds sampled at 8 kHz and calculating the sum of squared amplitudes of a shunt sound wave in a 50-msec interval at 10-msec intervals. Next, the maximum values of the blood flow sound power enclosed by the dotted circles in FIG. 5 are determined in Step 302 of detecting maximum values of the blood flow sound power. Furthermore, an average of the maximum values of the blood flow sound power in a given time interval (hereinafter referred to as a frame width) is determined in a predetermined interval (hereinafter referred to as a frame shift) in Step 303 of averaging the maximum values of the blood flow sound power. An example of average maximum values of blood flow sounds at a shunt site of a 30-minute dialysis patient is shown in FIG. 6, where the frame width is set at 30 seconds and the frame shift is set at 10 seconds. The waveform in FIG. 6 has been obtained as follows: the blood flow sounds at the shunt site are picked up by a chest piece 703 of a stethoscope, converted into an electrical signal by a condenser microphone 704, amplified by a microphone amplifier 705, converted into a digital signal by an A/D converter 706, and processed and calculated by a personal computer 707, as shown in FIG. 7. The abscissa in FIG. 6 represents time and the ordinate represents the logarithm of average maximum values of the blood flow sound power. Besides the stethoscope according to the present embodiment, preferable sound wave detectors include, for example, a small, lightweight conduction microphone or silicon microphone whose contact area and contact pressure are resistant to fluctuations caused by shape or motion of a contact site of a human body. Incidentally although in FIG. 7, the maximum values of the blood flow sound power are calculated from a digital signal of the blood flow sounds by a personal computer, the blood flow sounds may be converted into blood flow sound power or into maximum values of blood flow sound power as an analog signal by an electrical circuit and subsequently converted into a digital signal and subjected to necessary processing.

Figure 8:
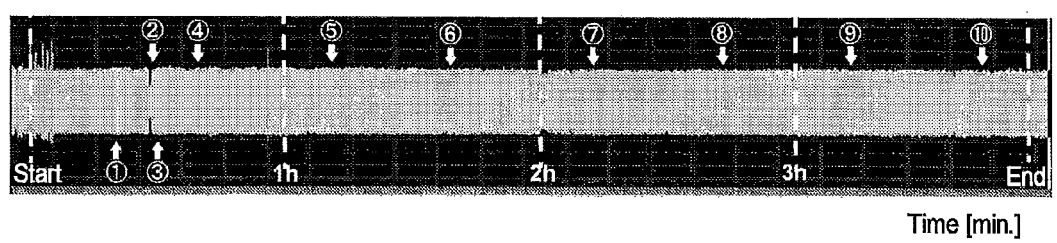
FIG. 8 is a diagram showing an example of blood flow sounds of a patient from start to end of dialysis.
Figure 9:
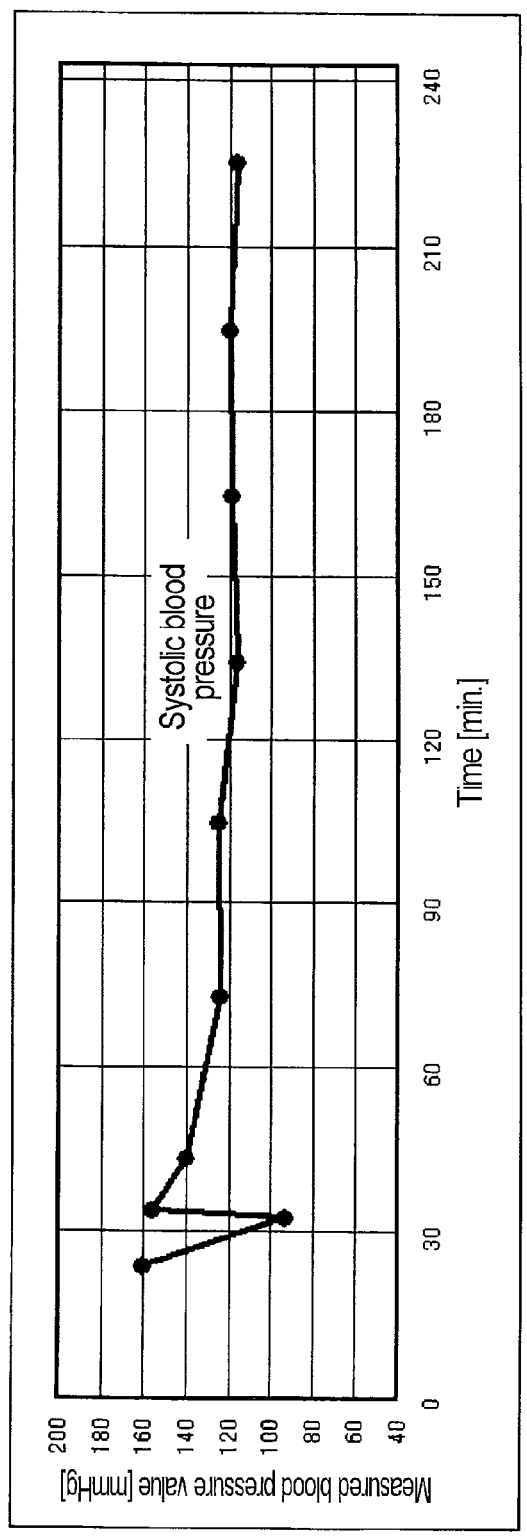
FIG. 9 is a graph showing blood pressure values measured intermittently by an oscillometric method.
Figure 10:
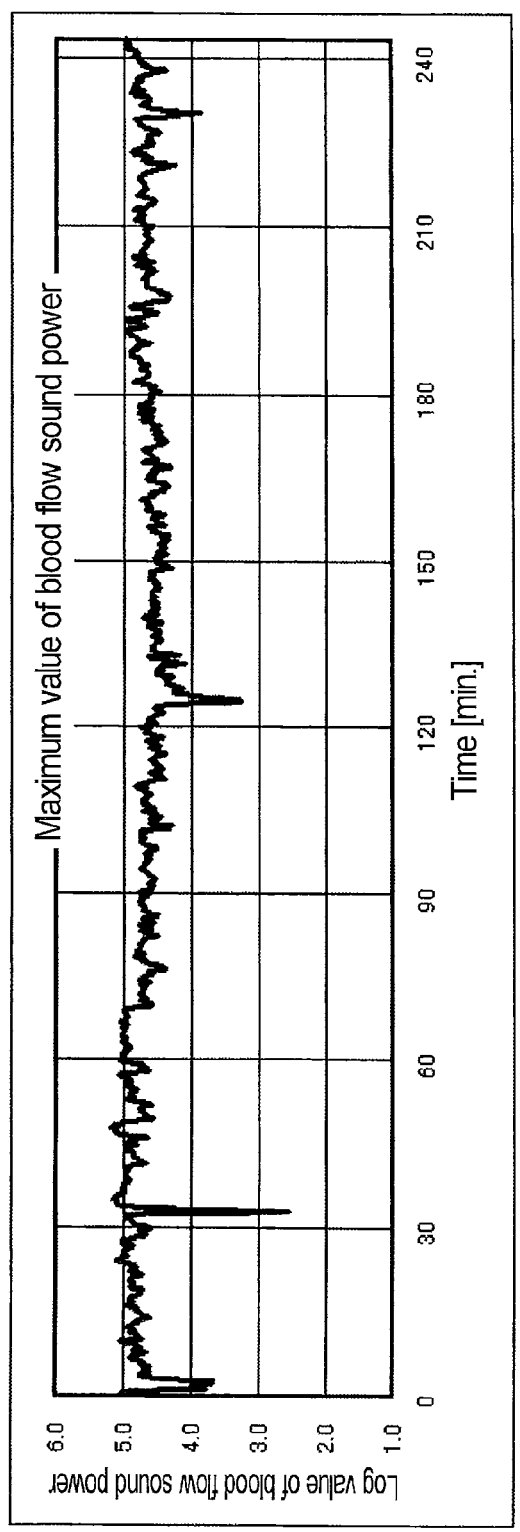
FIG. 10 is a graph showing changes in maximum values of blood flow sound power determined from the blood flow sounds in FIG. 8.

A blood flow sound wave of a dialysis patient (hereinafter referred to as dialysis patient 1) during the time of dialysis is shown in FIG. 8 and ten measurements of blood pressure values taken intermittently by an oscillometric method are shown in FIG. 9. FIG. 10 shows results produced by processing the blood flow sound wave in FIG. 8 using the process flow in FIG. 3. Specifically, FIG. 10 shows a logarithmic plot of averaged maximum values of blood flow sound power obtained by extracting a frequency band between 0.75 kHz and 1.75 kHz from blood flow sounds sampled at 8 kHz and calculating the sum of squared amplitudes of a shunt sound wave in a 50-msec interval at 10-msec intervals, where a frame width of 30 seconds and a frame shift of 10 seconds are used for averaging. Incidentally, the sharp fall in the blood pressure 30 minutes after the start of dialysis was caused by a Valsalva test.

Figure 11:
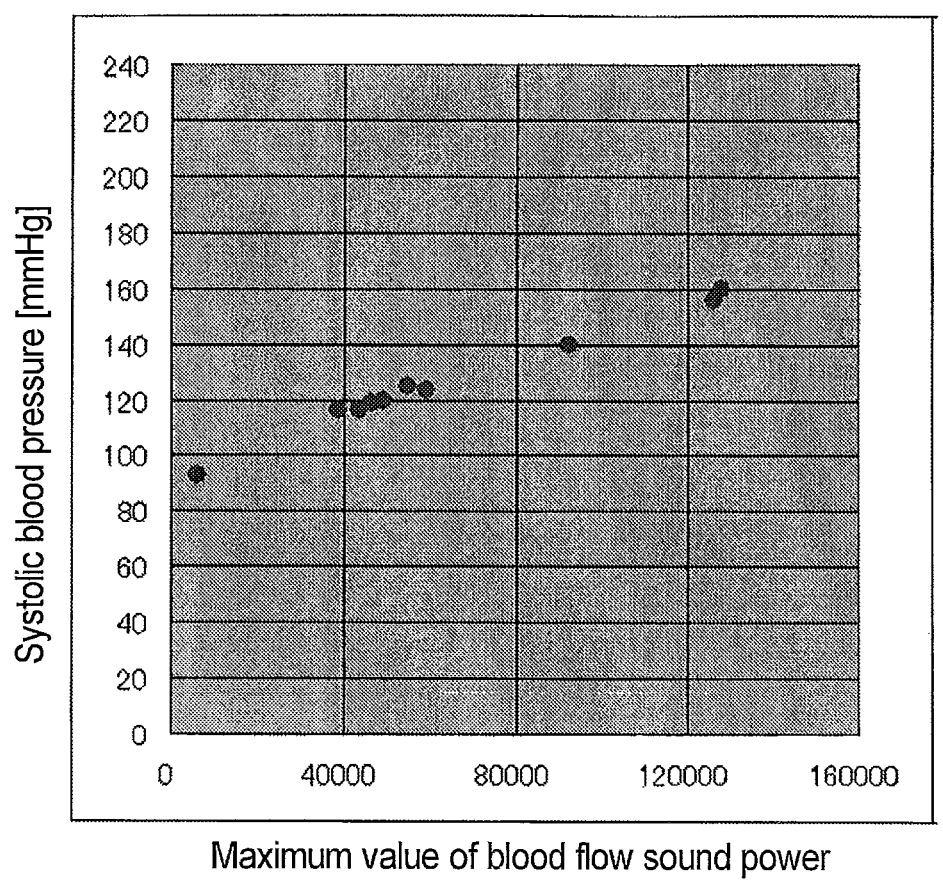
FIG. 11 is a correlation diagram between systolic blood pressure and maximum value of blood flow sound power.

FIG. 11 is a scatter diagram of the systolic blood pressure in FIG. 9 vs. the maximum value (30-second average) of blood flow sound power which corresponds in time to the systolic blood pressure. Also, a correlation coefficient between the systolic blood pressure and the maximum value of blood flow sound power is calculated to be 0.99, indicating a high correlation. Therefore, if multiple measurements of blood pressure values and maximum values of blood flow sound power at corresponding times are known and if regression lines for the systolic blood pressure and the maximum values of blood flow sound power can be calculated, the systolic blood pressure can be estimated from the maximum values of blood flow sound power. The present invention relates to an apparatus designed to calculate a systolic blood pressure estimation linear function which corresponds to a regression line from a single measurement of blood pressure values, blood flow sound power at the corresponding time, and a standard pulse wave waveform and estimate systolic blood pressure from the maximum value of blood flow sound power.

Figure 12:
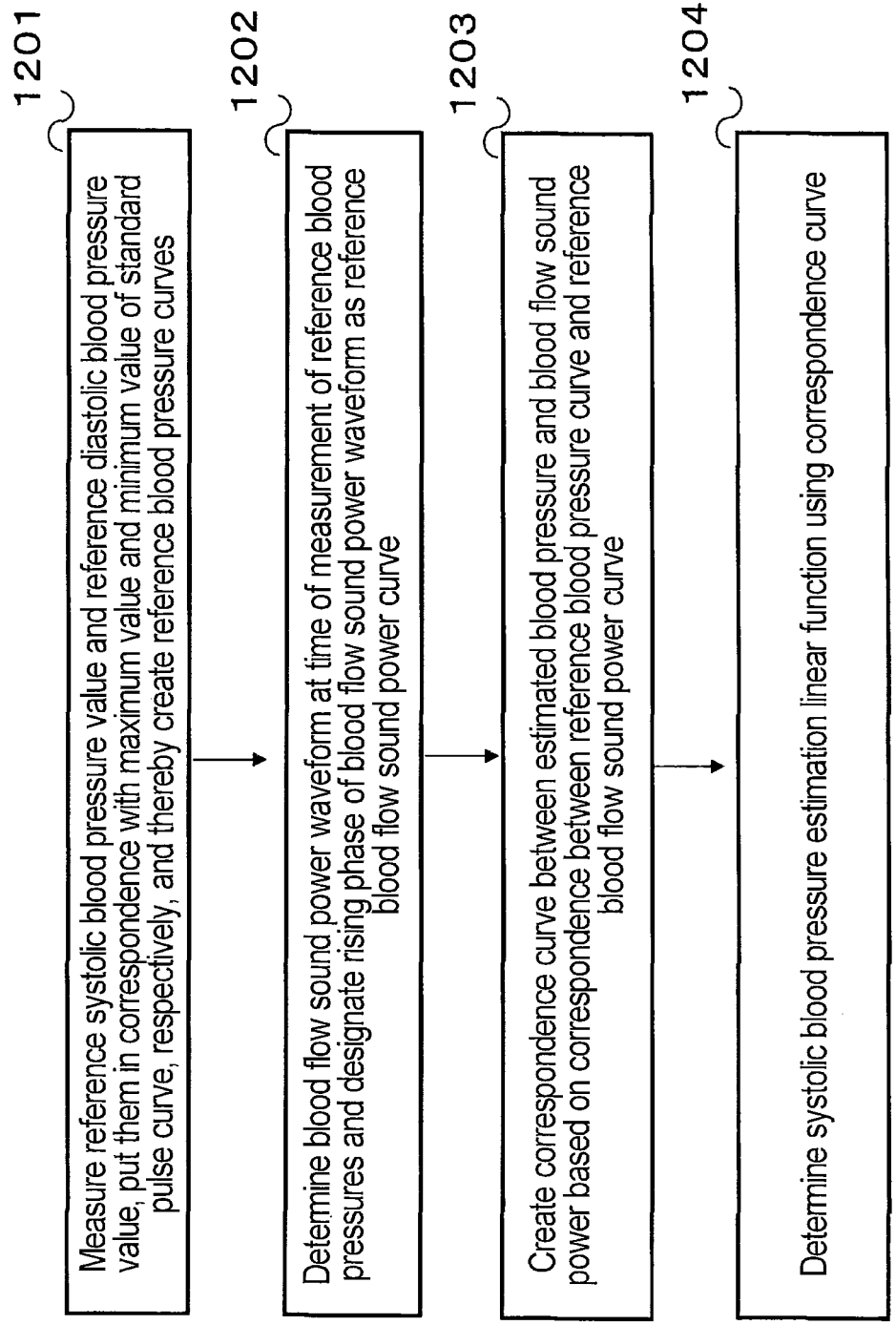
FIG. 12 is a calculation flow diagram of a systolic blood pressure estimation linear function.
Figure 13:
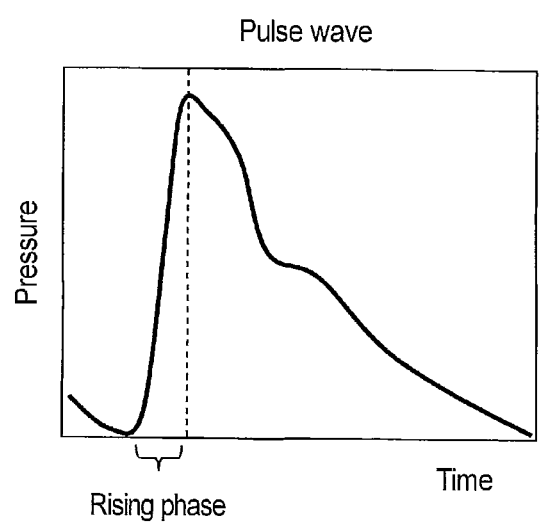
FIG. 13 is a diagram showing a pulse wave.
Figure 14:
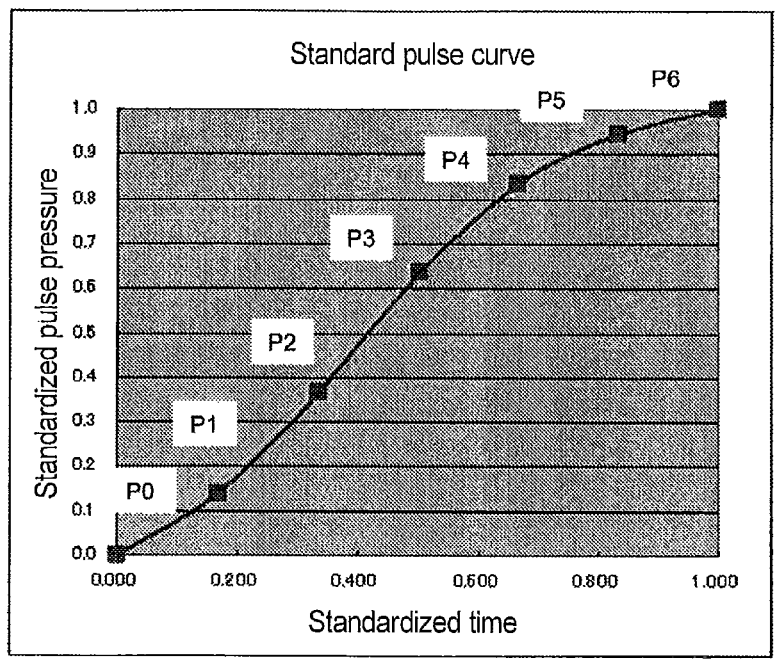
FIG. 14 is a graph showing a standard pulse curve.

FIG. 12 shows a process flow for calculating the systolic blood pressure estimation linear function from a single measurement of reference blood pressure values (reference systolic blood pressure value and reference diastolic blood pressure value), a reference blood flow sound power waveform at the corresponding time, and a standard pulse curve. As a precondition, a rising phase is cut out from a pulse wave such as shown in FIG. 13 in advance and a waveform is prepared by being standardized such that the highest value and lowest value will be 0 and 1, respectively, both in a time axis direction and in a pressure direction as shown in FIG. 14 (hereinafter referred to as a standard pulse curve). The pulse wave can be measured using a measuring device such as BP-608E made by OMRON COLIN Co., Ltd. Preferably a standard pulse curve is prepared for each subject whose blood pressure will be estimated. However, this is not practical because BP-608E is not used commonly. Besides, the waveform in the rising phase of a pulse wave does not vary significantly from person to person. Therefore, the rising phases of pulse waves of multiple persons measured in advance may be averaged and used as the standard pulse curve.

Figure 15:
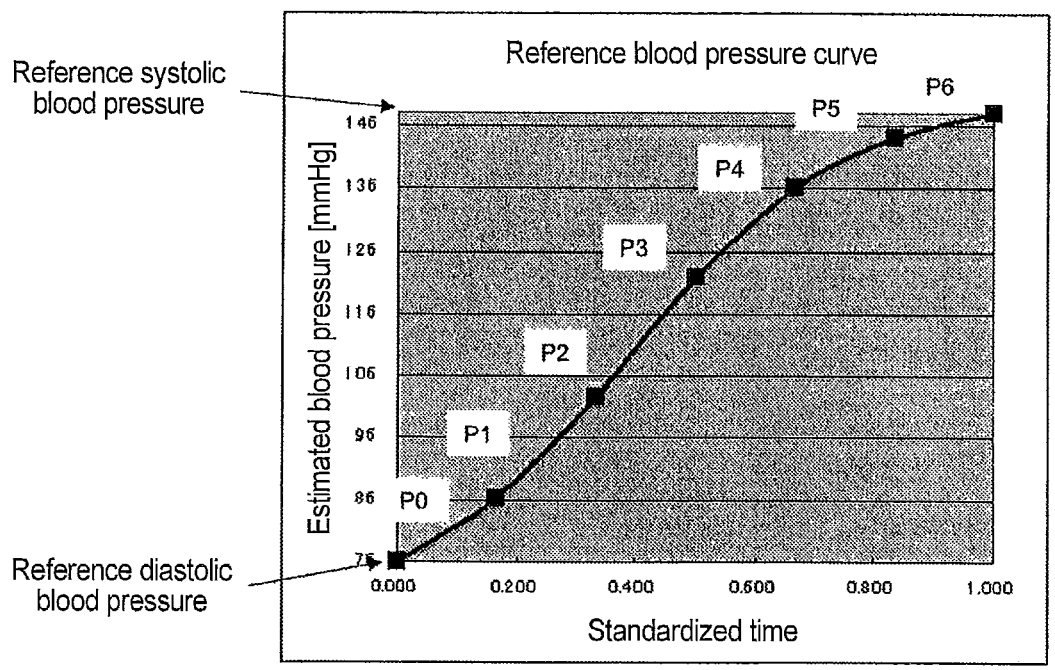
FIG. 15 is a graph showing a reference blood pressure curve.

First, in Step 1201, the reference systolic blood pressure value is put in correspondence with a pulse pressure value of 1.0 which is the maximum value of standardized pulse pressure values of the standard pulse curve and the reference diastolic blood pressure value is put in correspondence with a pulse pressure value of 0.0 which is the minimum value of standardized pulse pressure values of the standard pulse curve, as shown in FIG. 15. As shown in FIG. 13, the pulse wave shows changes in blood pressure, but does not contain blood pressure values. Thus, a reference diastolic blood pressure value and reference systolic blood pressure value, both measured separately, are fitted in the graph as a maximum value and minimum value of the pulse wave to give blood pressure values to the pulse wave. That is, if the pulse wave before being put in correspondence (standard pulse curve) is denoted by p and the pulse wave after being put in correspondence (reference blood pressure curve) is denoted by P, $$P = \text{(reference diastolic blood pressure value)} + \text{(reference systolic blood pressure value} - \text{reference diastolic blood pressure value)} \times p$$

Hereinafter, the standard pulse curve associated with reference blood pressure values is referred to as a reference blood pressure curve.

Figure 16:
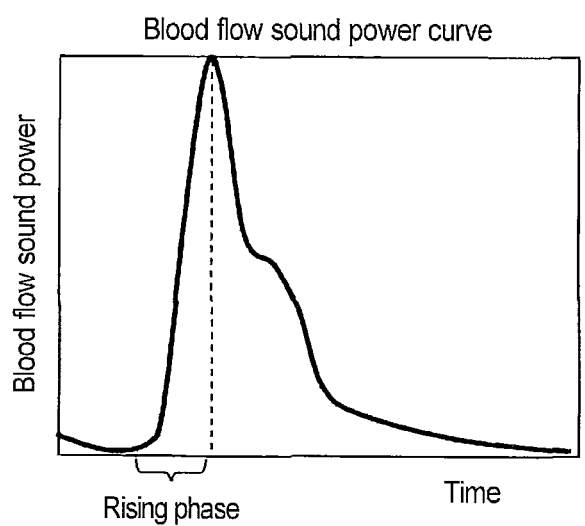
FIG. 16 is a schematic diagram of a relationship between blood flow sound power waveform and time.
Figure 17:
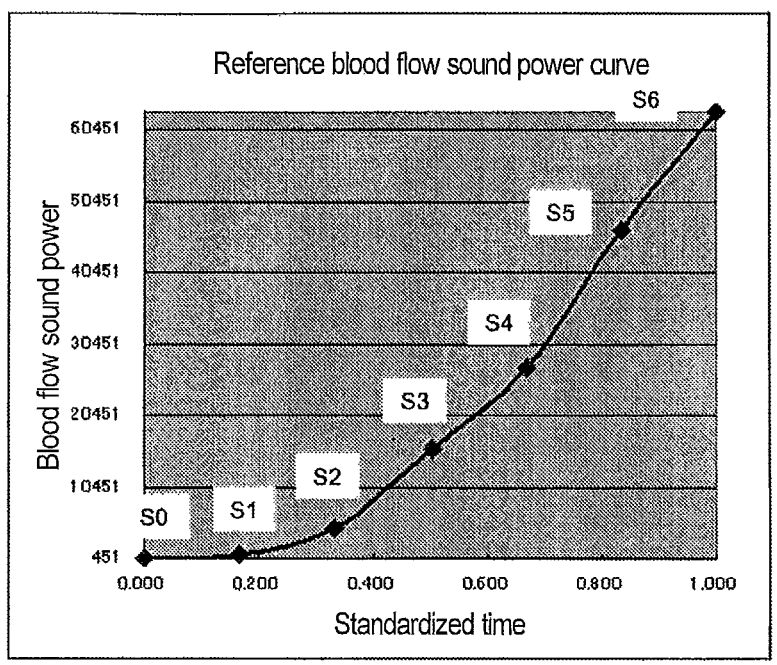
FIG. 17 is a graph showing a reference blood flow sound power curve.

Next, in Step 1202, using the process flow shown in FIG. 3, a blood flow sound power waveform at the time corresponding to the time of measurement of reference blood pressure values such as shown in FIG. 16 is determined and the rising phase of the blood flow sound power waveform is cut out. In so doing, the waveform obtained by cutting out the rising phase is standardized with respect to the abscissa, i.e., the time axis, such that the highest value and lowest value will be 0 and 1, respectively, as shown in FIG. 17. The resulting curve is referred to hereinafter as a reference blood flow sound power curve. Incidentally, the blood flow sound power waveform at the time corresponding to the time of measurement of reference blood pressure values may be an average of blood flow sound power waveforms measured during measurement of the reference blood pressure or a blood flow sound power waveform generated at the time of measurement of the reference systolic blood pressure and identified using an apparatus shown in FIG. 45.

Figure 18:
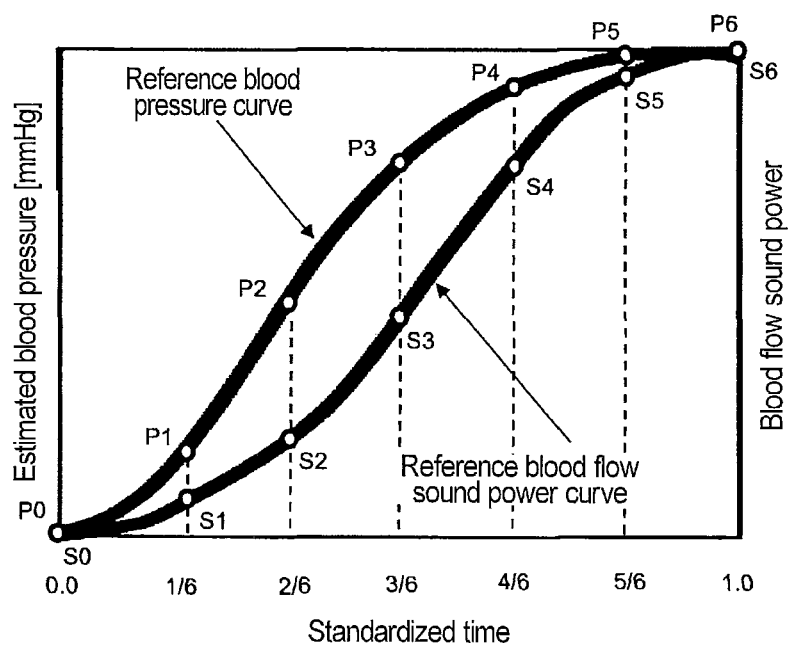
FIG. 18 is a graph showing a reference blood pressure curve and reference blood flow sound power curve superimposed over each other along a common standardized time.
Figure 19:
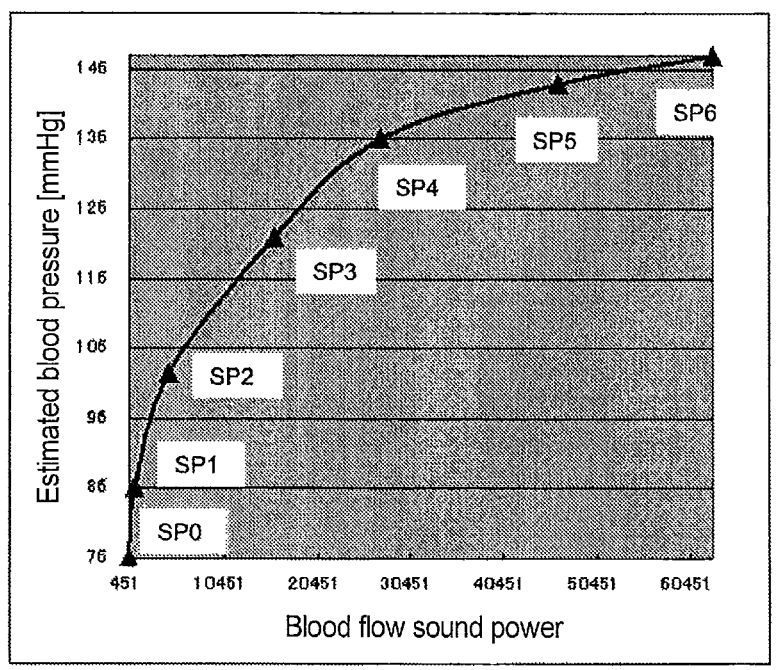
FIG. 19 is a graph showing a correspondence curve between estimated blood pressure and blood flow sound power.

Furthermore, in Step 1203, blood flow sound power is plotted on the abscissa and estimated blood pressure is plotted on the ordinate by bringing the value of the reference blood pressure curve and the value of the blood flow sound power at each standardized time point between 0.0 to 1.0 into correspondence with each other. As an example, the reference blood pressure curve in FIG. 15 and reference blood flow sound power curve in FIG. 17, when superimposed over each other as shown in FIG. 18 and put in correspondence with each other at each standardized time point, provides a correspondence curve between estimated blood pressure and blood flow sound power in a period of common standardized time as shown in FIG. 19. In this case, since P0 in FIG. 15 and S0 in FIG. 17 represent the estimated blood pressure and blood flow sound power both at the start time 0 of the standardized time, the estimated blood pressure and blood flow sound power are plotted as SP0 in FIG. 19. Similarly, pairs P1 and S1, P2 and S2, P3 and S3, P4 and S4, P5 and S5, and P6 and S6 of the estimated blood pressure in FIG. 15 and blood flow sound power in FIG. 17 are plotted as SP1, SP2, SP3, SP4, SP5, and SP6 at time points 1/6, 2/6, 3/6, 4/6, 5/6, and 1 of the standardized time in FIG. 19.

According to the present invention, since there is a high positive correlation between systolic blood pressure values and maximum values of blood flow sound power, assuming that the relationship between the two is given by a linear function as follows, $$\text{Estimated systolic blood pressure} = a \times \text{maximum value of blood flow sound power} + b \quad \text{Eq. (1)}$$

the systolic blood pressure estimation linear function is calculated by calculating a slope a (>0) and Y intercept b using the correspondence curve between blood pressure and blood flow sound power in FIG. 19.

According to the present embodiment, blood pressure measurements are taken multiple times, and the first measured blood pressure values are used as reference blood pressure values for calculation of the systolic blood pressure estimation linear function while the second and subsequent measured blood pressure values are used for evaluation of estimated blood pressure values at the corresponding time. The time of the first blood pressure measurement is referred to as reference time point, and the systolic blood pressure value and maximum value of blood flow sound power at the reference time point are referred to as a reference blood pressure value and reference blood flow sound power value, respectively. The reference blood flow sound power value corresponds, for example, to the blood flow sound power value SP6 in the correspondence curve of FIG. 19. Regarding the systolic blood pressure estimation linear function, according to the present embodiment, a first systolic blood pressure estimation linear function for the subject and a second systolic blood pressure estimation linear function for the subject are calculated, where according to the first systolic blood pressure estimation linear function for the subject, the maximum value of the blood flow sound power during blood pressure estimation falls below the reference blood flow sound power value and according to the second systolic blood pressure estimation linear function for the subject, the maximum value of the blood flow sound power during blood pressure estimation rises above the reference blood flow sound power value, and the estimated systolic blood pressure is determined using the first systolic blood pressure estimation linear function or the second systolic blood pressure estimation linear function depending on variations in the maximum value of the blood flow sound power of the subject undergoing the blood pressure estimation. In the case where the maximum value of the blood flow sound power falls during blood pressure estimation, the estimated systolic blood pressure is determined using another systolic blood pressure estimation linear function instead of the first systolic blood pressure estimation linear function if the maximum value of the blood flow sound power of the subject during the blood pressure estimation falls to or below the threshold.

<Blood Pressure Estimation Method for Use when the Maximum Value of Blood Flow Sound Power During Blood Pressure Estimation Becomes Smaller than the Reference Blood Flow Sound Power Value>

In this Case, the First Systolic Blood Pressure estimation linear function is defined by a line which has a slope joining a point existing between 5/12 and 7/12 (both inclusive) of the standardized time and a point existing between 9/12 and 11/12 (both inclusive) of the standardized time when a start point and end point of the standardized time on the blood pressure/blood flow sound power correspondence curve are taken as 0 and 1, respectively. For example, a slope around the middle of the blood pressure/blood flow sound power correspondence curve in FIG. 19, specifically, a slope on both sides of that point on the blood pressure/blood flow sound power correspondence curve which corresponds to an intermediate point 0.5 of the standardized time or a slope of a line joining two points on the blood pressure/blood flow sound power correspondence curve passing through the intermediate point is designated as the slope a of Eq. (1), and the Y intercept b is determined such that Eq. (1) will pass through that point on the blood pressure/blood flow sound power correspondence curve which corresponds to the end point of the standardized time. For example, in FIG. 19, if coordinates of SP0, SP1, SP2, SP3, SP4, SP5, SP6 are (s0,p0), (s1,p1), (s2,p2), (s3,p3), (s4,p4), (s5,p5), and (s6,p6), a slope a1 and Y intercept b1 are given by $$a1 = (p5-p3)/(s5-s3) \quad \text{Eq. (2)}$$

$$b1 = p6 - a1 \times s6 \quad \text{Eq. (3)}$$

and the first systolic blood pressure estimation linear function is given by $$\text{Estimated systolic blood pressure} = a1 \times \text{maximum value of blood flow sound power} + b1 \quad \text{Eq. (4)}$$

Figure 20:
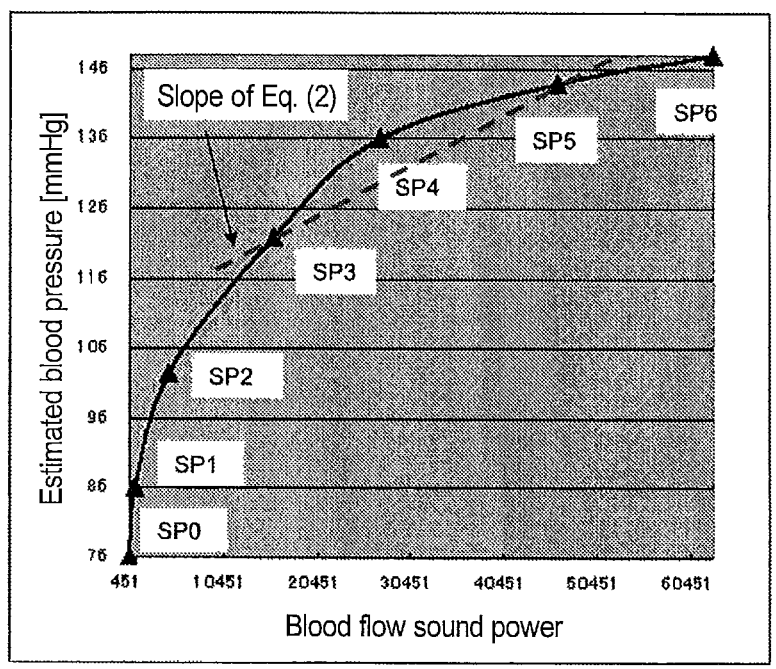
FIG. 20 is a graph showing a slope of a first systolic blood pressure estimation linear function.
Figure 21:
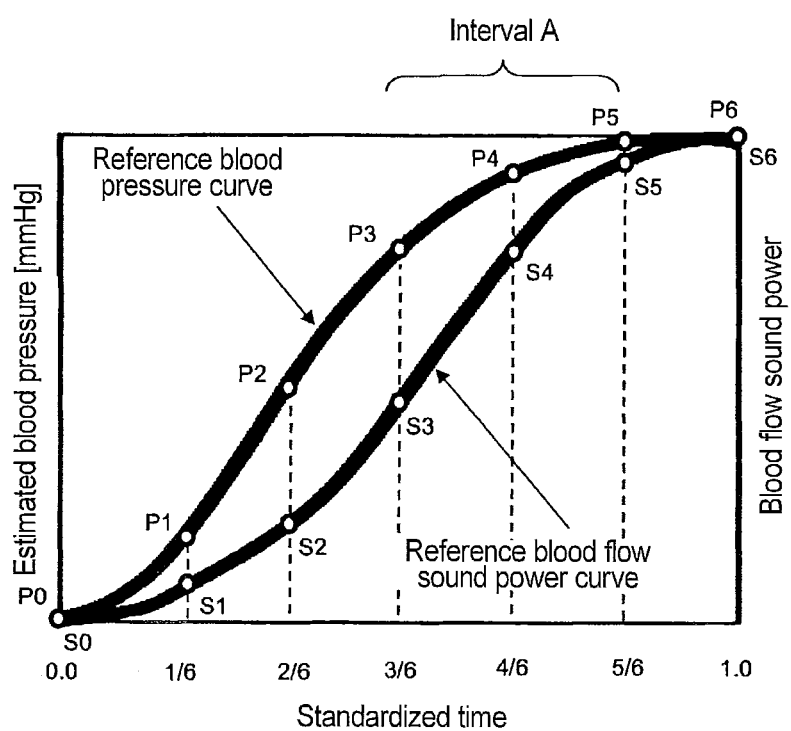
FIG. 21 is a graph showing an interval used to determine the slope of the first systolic blood pressure estimation linear function during the standardized time.

The slope a1 is shown in FIG. 20. This means that a ratio between an increase in the blood flow sound power and increase in blood pressure in interval A in FIG. 21 is used as the slope a1 of the first systolic blood pressure estimation linear function.

Figure 22:
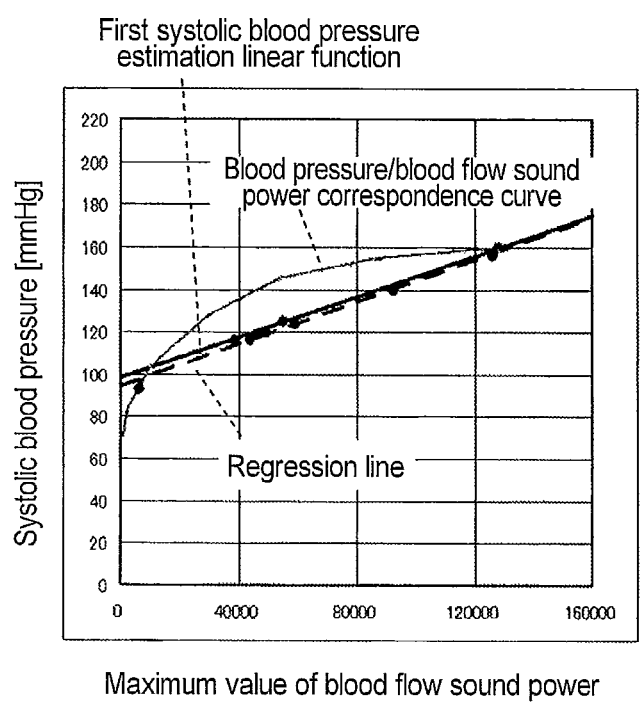
FIG. 22 is a graph showing a first systolic blood pressure estimation linear function, regression line, and blood pressure/blood flow sound power correspondence curve of dialysis patient 1.
Figure 23:
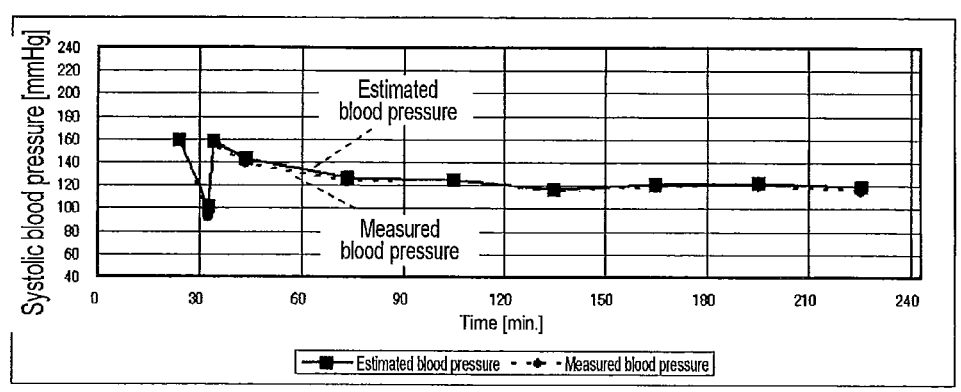
FIG. 23 is a graph showing correspondence between actually measured blood pressure values and estimated blood pressure values of dialysis patient 1.

FIG. 22 is a graph showing the scatter diagram of the maximum value of blood flow sound power vs. systolic blood pressure of dialysis patient 1 in FIG. 11, together with a regression line, a blood pressure/blood flow sound power correspondence curve, and the first systolic blood pressure estimation linear function of Eq. (4). In the case of dialysis patient 1, as can be seen from FIG. 10, the first systolic blood pressure estimation linear function of Eq. (4) is applicable to a range covering the reference time point and almost all subsequent time points, meaning that the first systolic blood pressure estimation linear function of Eq. (4) nearly approximates the regression line. FIG. 23 is a graph comparing estimated systolic blood pressure with actually measured blood pressure values at ten time points, where the systolic blood pressure was estimated from the maximum value of blood flow sound power using Eq. (4). Thus, it can be seen that the estimated blood pressure almost follows the measured blood pressure including the fall in the blood pressure caused by the Valsalva test conducted 30 minutes after the start of dialysis. This demonstrates the effectiveness of the blood pressure estimation apparatus according to the present invention.

Figure 24:
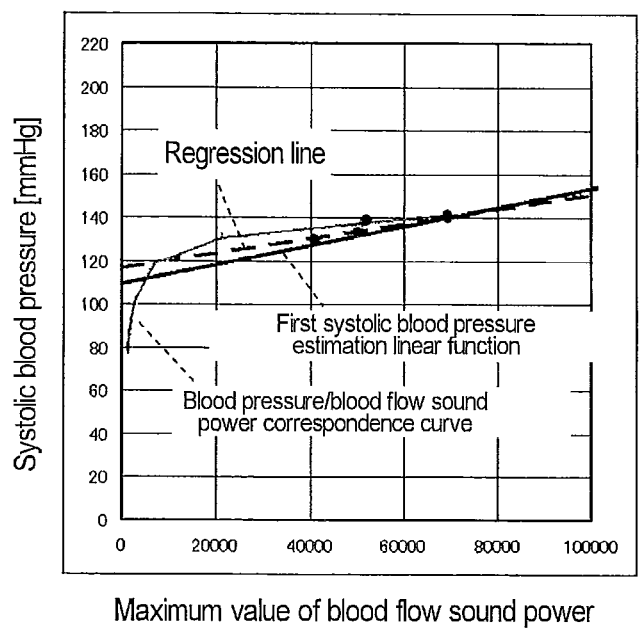
FIG. 24 is a graph showing a first systolic blood pressure estimation linear function, regression line, and blood pressure/blood flow sound power correspondence curve of dialysis patient 2.
Figure 25:
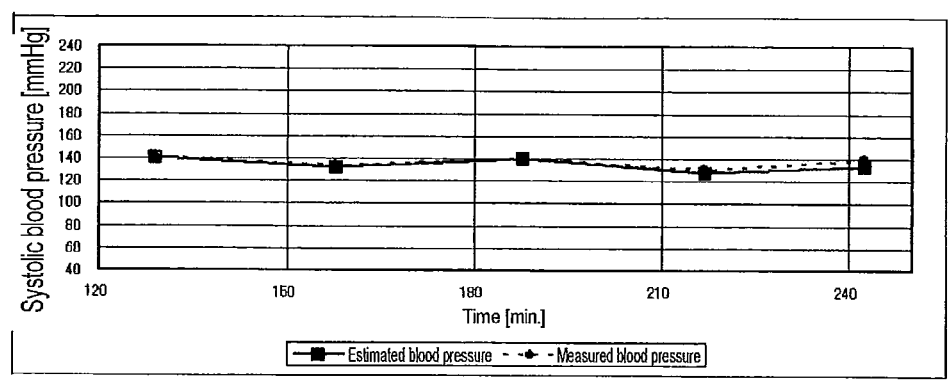
FIG. 25 is a graph showing correspondence between actually measured blood pressure values and estimated blood pressure values of dialysis patient 2.
Figure 26:
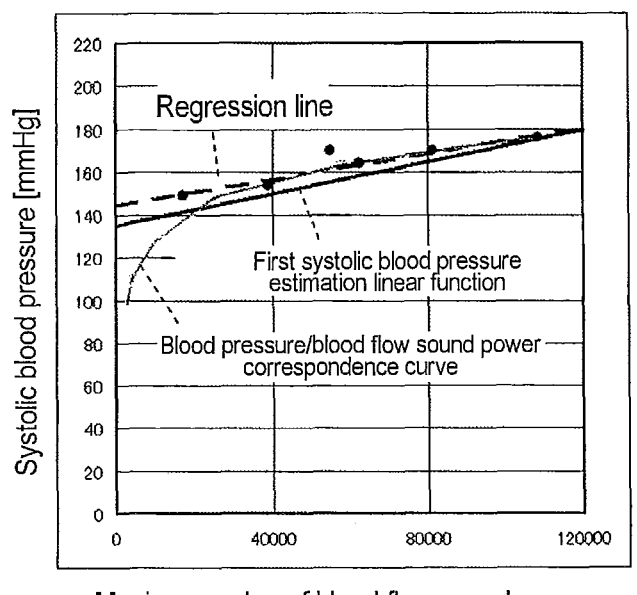
FIG. 26 is a graph showing a first systolic blood pressure estimation linear function, regression line, and blood pressure/blood flow sound power correspondence curve of dialysis patient 3.
Figure 27:
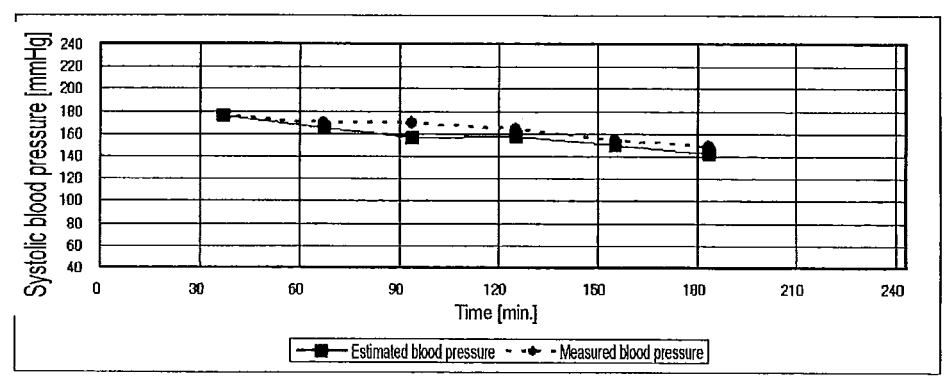
FIG. 27 is a graph showing correspondence between actually measured blood pressure values and estimated blood pressure values of dialysis patient 3.

FIG. 24 is a graph of another dialysis patient (hereinafter referred to as dialysis patient 2), showing a scatter diagram of the maximum value of blood flow sound power vs. systolic blood pressure, together with a regression line, a blood pressure/blood flow sound power correspondence curve, and the first systolic blood pressure estimation linear function of Eq. (4). FIG. 25 is a graph comparing estimated blood pressure values obtained using Eq. (4) with measured blood pressure values. FIG. 26 is a graph of still another dialysis patient (hereinafter referred to as dialysis patient 3), showing a scatter diagram of the maximum value of blood flow sound power vs. systolic blood pressure, together with a regression line, a blood pressure/blood flow sound power correspondence curve, and the first systolic blood pressure estimation linear function of Eq. (4). FIG. 27 is a graph comparing estimated blood pressure values obtained using Eq. (4) with measured blood pressure values. Thus, it can be seen that blood pressure estimation using the first systolic blood pressure estimation linear function of Eq. (4) is effective for patients in whom the maximum value of blood flow sound power after standardization becomes smaller than the reference blood flow sound power value, i.e., for patients whose blood pressure falls gradually during dialysis (during blood pressure estimation).

<Blood Pressure Estimation Method for Use when the Maximum Value of Blood Flow Sound Power During Blood Pressure Estimation Becomes Larger than the Reference Blood Flow Sound Power Value>

When the maximum value of blood flow sound power during blood pressure estimation becomes larger than the reference blood flow sound power value, a second systolic blood pressure estimation linear function is used. The second systolic blood pressure estimation linear function is defined by a line which has a slope joining a point corresponding to the end point of the standardized time on the blood pressure/blood flow sound power correspondence curve and a point existing between 9/12 and 11/12 (both inclusive) of the standardized time when the start point and end point of the standardized time are taken as 0 and 1, respectively. For example, an extension line of that point on the blood pressure/blood flow sound power correspondence curve which corresponds to the end point of the standardized time is used as the second systolic blood pressure estimation linear function. For example, in FIG. 19, a slope a2 and Y intercept b2 are given by $$a2=(p6-p5)/(s6-s5) \quad \text{Eq. (5)}$$

$$b2=p6-a2 \times s6 \quad \text{Eq. (6)}$$

and the second systolic blood pressure estimation linear function for use when the maximum value of blood flow sound power is larger than the reference power value is given by $$\text{Estimated systolic blood pressure}=a2 \times \text{maximum value of blood flow sound power}+b2 \quad \text{Eq. (7)}$$

Figure 28:
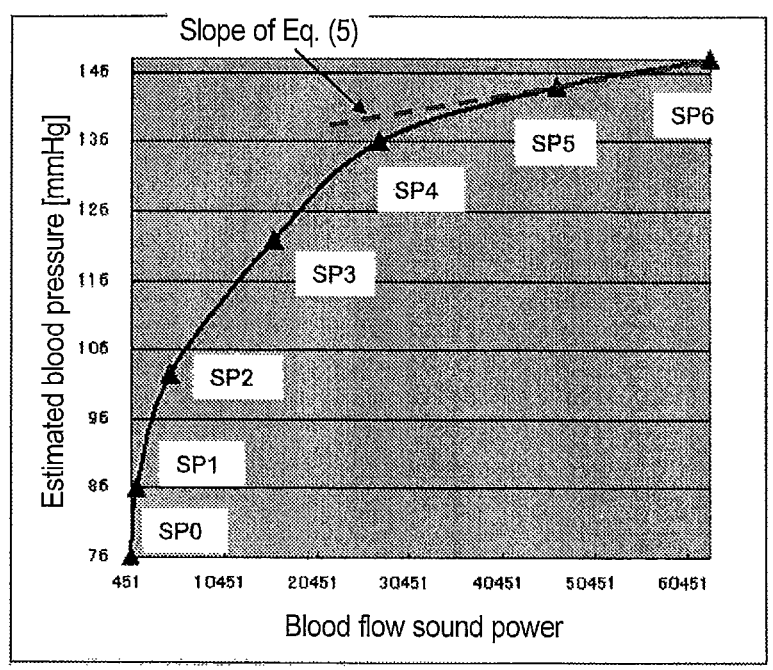
FIG. 28 is a graph showing a slope of a second systolic blood pressure estimation linear function.
Figure 29:
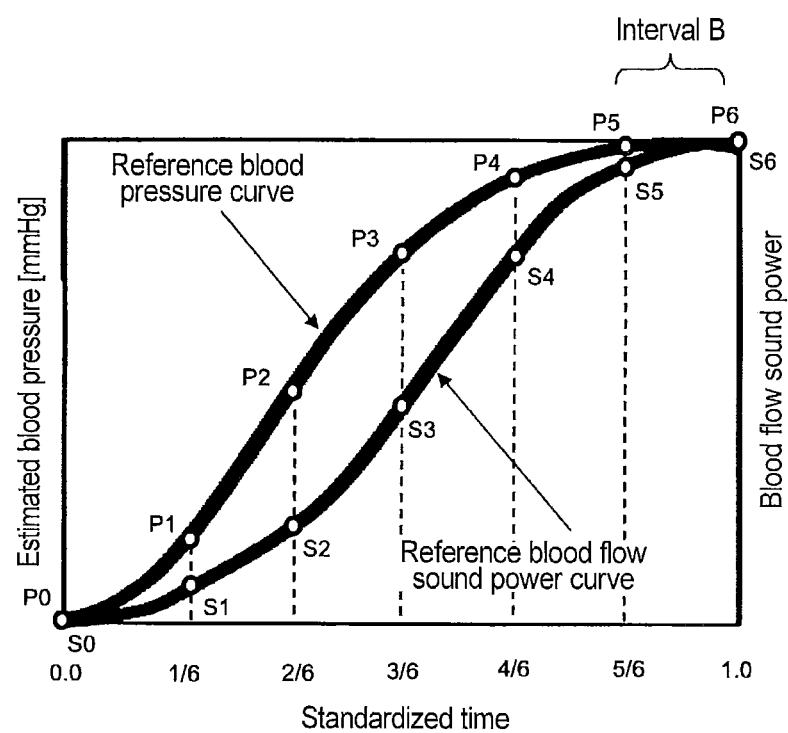
FIG. 29 is a graph showing an interval used to determine the slope of the second systolic blood pressure estimation linear function during the standardized time.

The slope a2 is shown in FIG. 28. This means that a ratio between an increase in the blood flow sound power and increase in blood pressure in interval B in FIG. 29 is used as the slope a2 of the second systolic blood pressure estimation linear function.

Figure 30:
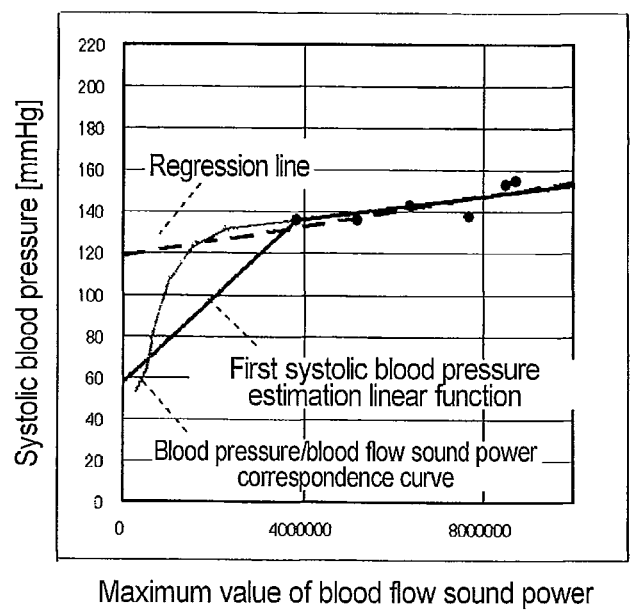
FIG. 30 is a graph showing a second systolic blood pressure estimation linear function, regression line, and blood pressure/blood flow sound power correspondence curve of dialysis patient 4.
Figure 31:
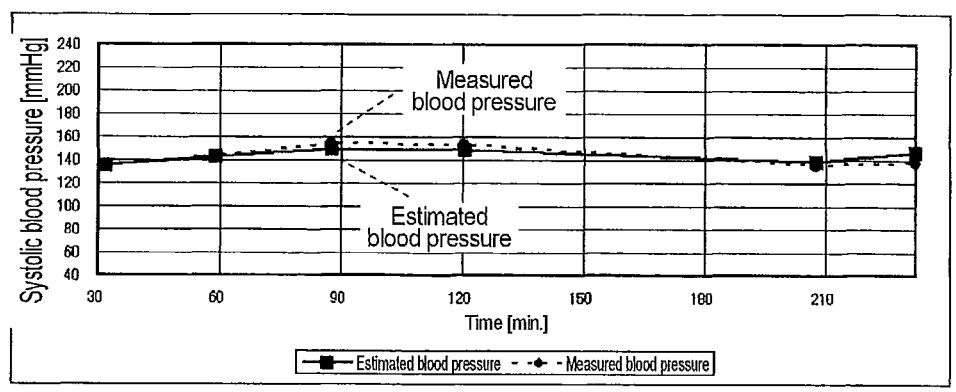
FIG. 31 is a graph showing correspondence between actually measured blood pressure values and estimated blood pressure values of dialysis patient 4.
Figure 32:
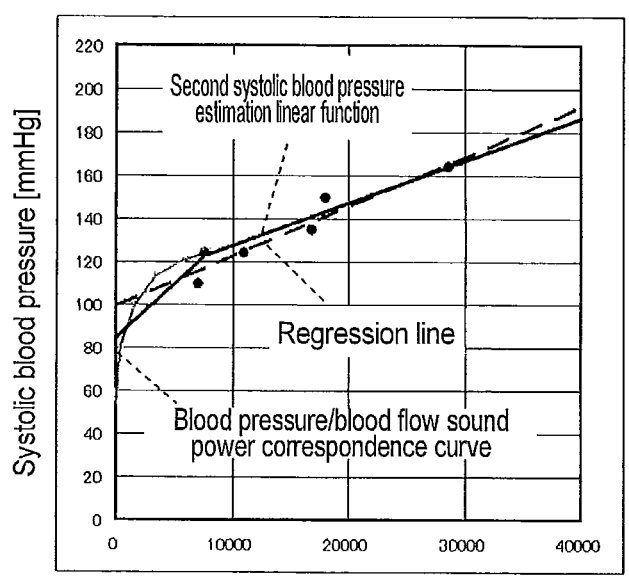
FIG. 32 is a graph showing a second systolic blood pressure estimation linear function, regression line, and blood pressure/blood flow sound power correspondence curve of dialysis patient 5.
Figure 33:
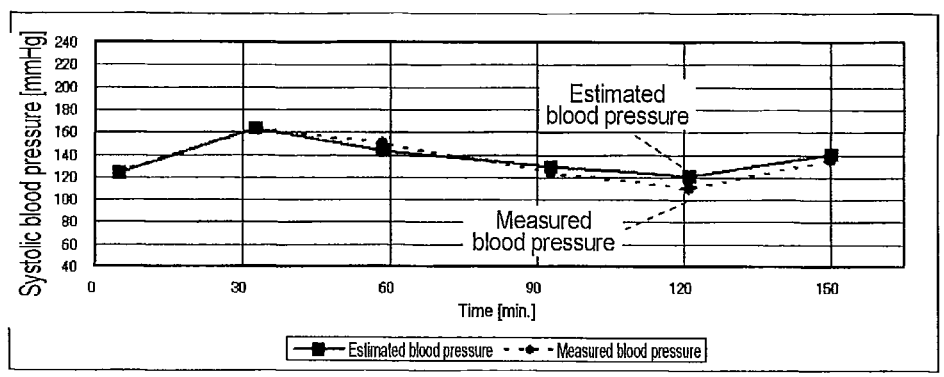
FIG. 33 is a graph showing correspondence between actually measured blood pressure values and estimated blood pressure values of dialysis patient 5.

FIG. 30 is a graph of a dialysis patient (hereinafter referred to as dialysis patient 4) in whom the maximum value of blood flow sound power becomes larger than the reference blood flow sound power value once after the reference time point, i.e., elevation of blood pressure is observed during dialysis, where the graph shows a scatter diagram of the maximum value of blood flow sound power vs. systolic blood pressure, together with a regression line, a blood pressure/blood flow sound power correspondence curve, and the second systolic blood pressure estimation linear function of Eq. (7). FIG. 31 is a graph comparing estimated blood pressure values obtained using Eq. (7) with measured blood pressure values. FIG. 32 is a graph of another dialysis patient (hereinafter referred to as dialysis patient 5) whose blood pressure tends to fluctuate during dialysis as in the case of patient 4, where the graph shows a scatter diagram of the maximum value of blood flow sound power vs. systolic blood pressure, together with a regression line, a blood pressure/blood flow sound power correspondence curve, and the second systolic blood pressure estimation linear function of Eq. (7). FIG. 33 is a graph comparing estimated blood pressure values obtained using Eq. (7) with measured blood pressure values. Thus, it can be seen that blood pressure estimation using the second systolic blood pressure estimation linear function of Eq. (7) is effective for dialysis patients in whom the maximum value of blood flow sound power after standardization becomes larger than the reference blood flow sound power value, i.e., elevation of blood pressure is observed during dialysis.

Therefore, it is useful for blood pressure estimation to switch between Eq. (4) and Eq. (7) according to the maximum value of blood flow sound power of the dialysis patient.

<Blood Pressure Estimation Method for Use when the Maximum Value of Blood Flow Sound Power During Blood Pressure Estimation is Disproportionately Smaller than the Reference Blood Flow Sound Power Value>

Figure 34:
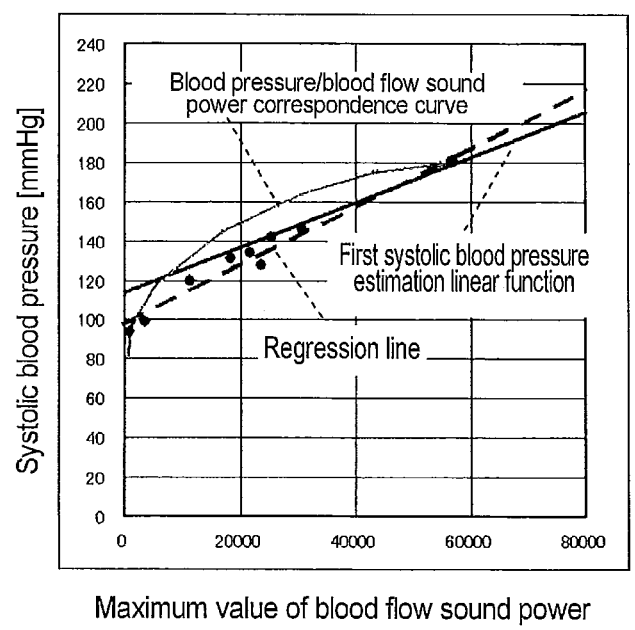
FIG. 34 is a graph showing a first systolic blood pressure estimation linear function, regression line, and blood pressure/blood flow sound power correspondence curve of dialysis patient 6.
Figure 35:
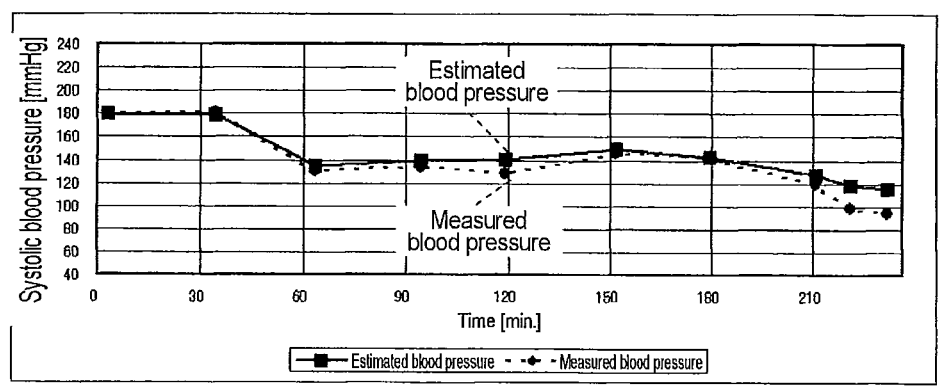
FIG. 35 is a graph showing correspondence between actually measured blood pressure values and estimated blood pressure values of dialysis patient 6.
Figure 36:
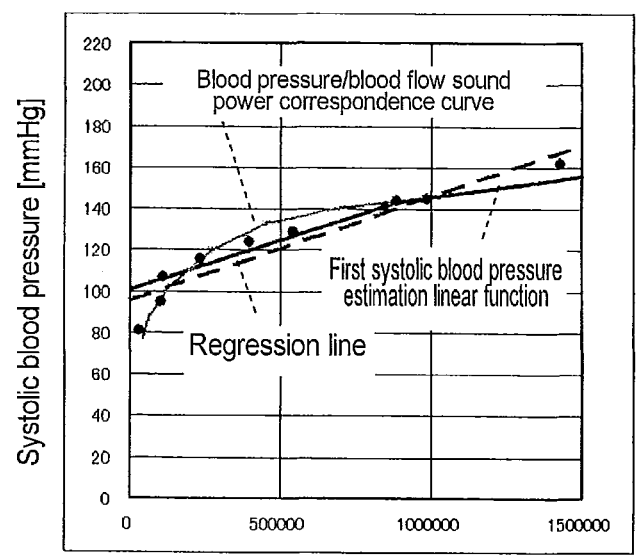
FIG. 36 is a graph showing a first systolic blood pressure estimation linear function, regression line, and blood pressure/blood flow sound power correspondence curve of dialysis patient 7.
Figure 37:
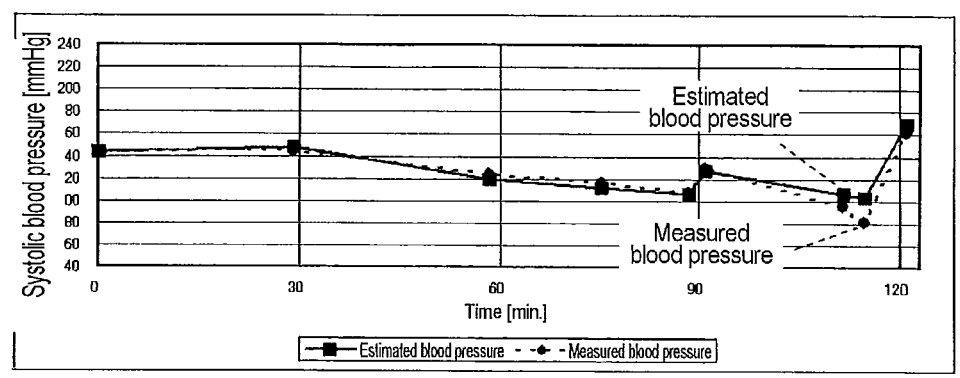
FIG. 37 is a graph showing correspondence between actually measured blood pressure values and estimated blood pressure values of dialysis patient 7.

One of the major uses of the blood pressure estimation apparatus according to the present invention is to detect sudden falls in blood pressure during dialysis (hereinafter referred to as dialytic hypotension). FIGS. 34 and 36 are graphs of two dialysis patients (hereinafter referred to as dialysis patient 6 and dialysis patient 7, respectively) who exhibit symptoms of dialytic hypotension, where the graphs show a scatter diagram of the maximum value of blood flow sound power vs. systolic blood pressure, together with a regression line, a blood pressure/blood flow sound power correspondence curve, and the first systolic blood pressure estimation linear function of Eq. (4), while FIGS. 35 and 37 are graphs comparing estimated blood pressure values with measured blood pressure values. As can be seen from FIGS. 34, 35, 36, and 37, when dialytic hypotension occurs, the maximum value of blood flow sound power may decrease to nearly 1/100 the reference blood flow sound power value and the systolic blood pressure may fall to about 80 mmHg, but the blood pressure estimation using the first systolic blood pressure estimation linear function of Eq. (4) cannot necessarily accommodate this situation sufficiently. In FIGS. 34 and 36, it can be seen that the plot of relationship between the maximum values of blood flow sound power and measured blood pressure values near the left end of the graph is located closer to the blood pressure/blood flow sound power correspondence curve than in the case of the first systolic blood pressure estimation linear function of Eq. (4). Therefore, in an interval in which the maximum value of blood flow sound power is very small and dialytic hypotension is suspected, it is considered that blood pressure can be estimated more accurately using an approximate function near the lower end of the blood pressure/blood flow sound power correspondence curve than using the first systolic blood pressure estimation linear function of Eq. (4). Thus, a threshold Sth for determination of a dialytic hypotension interval is established in advance for the maximum value of blood flow sound power, and when the maximum value of blood flow sound power falls below the threshold Sth, blood pressure is estimated using an approximate linear function (another systolic blood pressure estimation linear function) near the lower end of the blood pressure/blood flow sound power correspondence curve instead of the first systolic blood pressure estimation linear function of Eq. (4). For example, when the maximum value of blood flow sound power is equal to the threshold Sth, the another systolic blood pressure estimation linear function may have a point of intersection with the first systolic blood pressure estimation linear function and approximate the correspondence curve in a range in which the maximum value of the blood flow sound power is not above the threshold Sth. For example, the threshold Sth is set to s2 in FIG. 18, i.e., to 2/6 or less of the standardized time and when the maximum value of the blood flow sound power is smaller than s2, a slope a3 and Y intercept b3 are given by $$a3=(p2-p1)/(s2-s1) \quad \text{Eq. (8)}$$

$$b3=(a1 \times s2+b1)-a3 \times s2 \quad \text{Eq. (9)}$$

The another systolic blood pressure estimation linear function is given by

Estimated systolic blood pressure=$a3$×maximum value of blood flow sound power+$b3$  Eq. (10)

Figure 38:
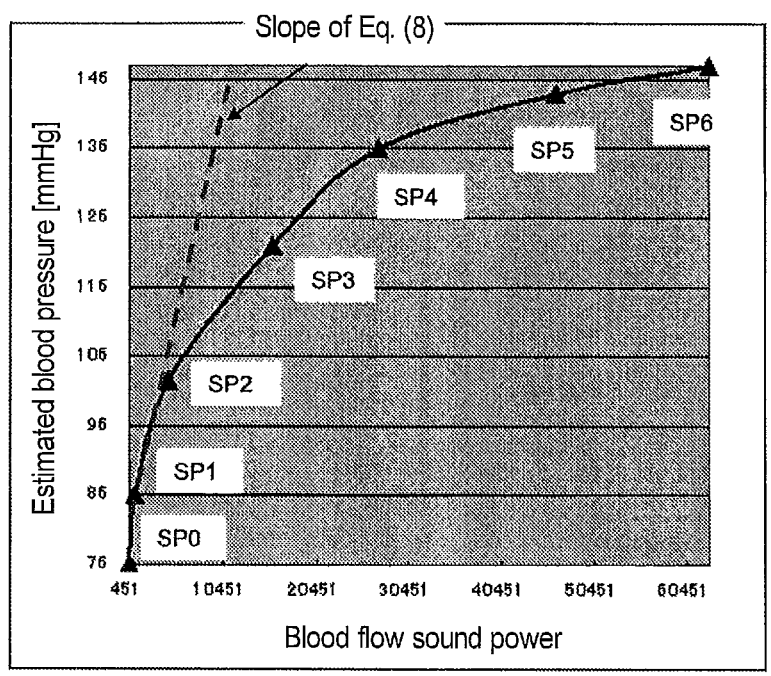
FIG. 38 is a graph showing a slope of another systolic blood pressure estimation linear function.
Figure 39:
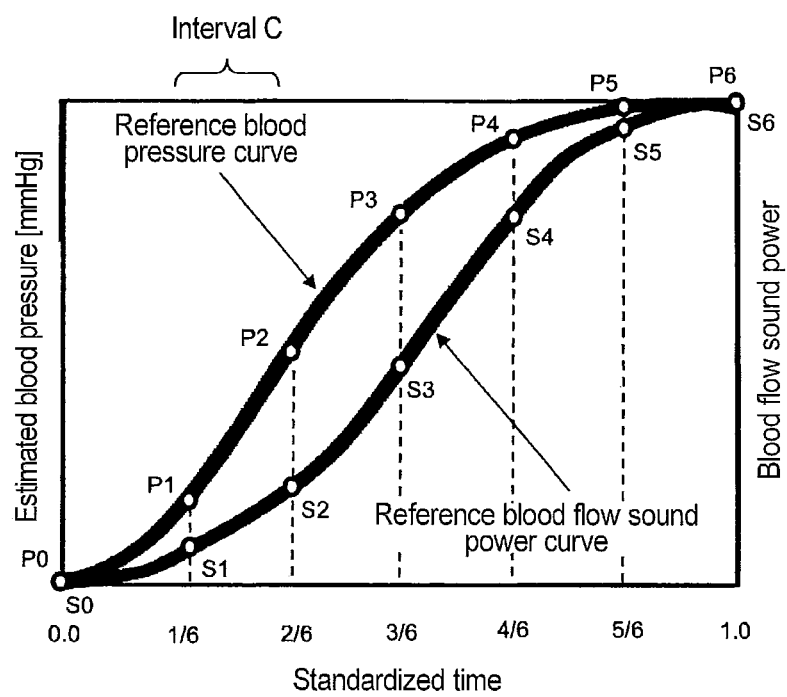
FIG. 39 is a graph showing an interval used to determine the slope of the another systolic blood pressure estimation linear function during the standardized time.

The slope a3 is shown in FIG. 38. This means that a ratio between an increase in the blood flow sound power and increase in blood pressure in interval C in FIG. 39 is used as the slope a3 of the another systolic blood pressure estimation linear function.

Figure 40:
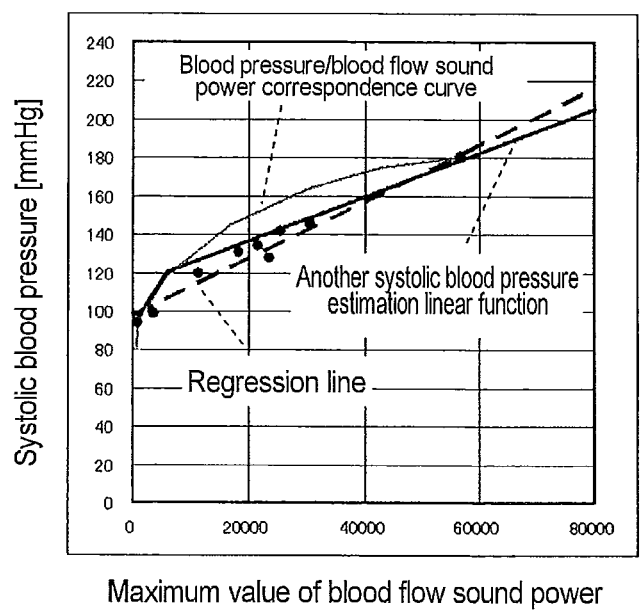
FIG. 40 is a graph showing another systolic blood pressure estimation linear function, regression line, and blood pressure/blood flow sound power correspondence curve of dialysis patient 6.
Figure 41:
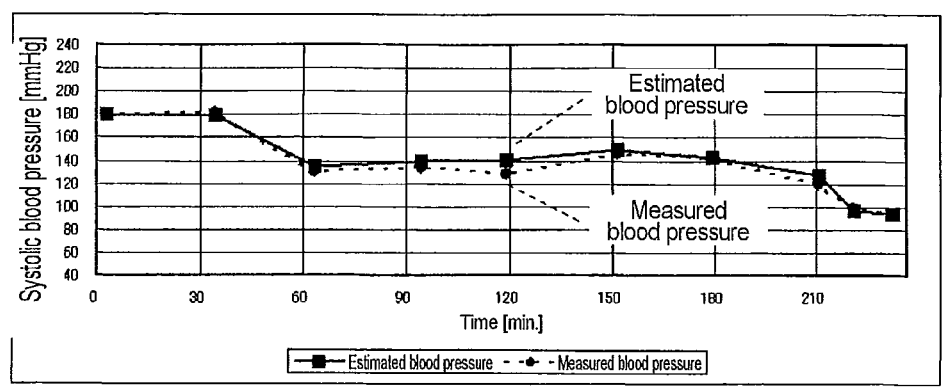
FIG. 41 is a graph showing correspondence between actually measured blood pressure values and estimated blood pressure values of dialysis patient 6.
Figure 42:
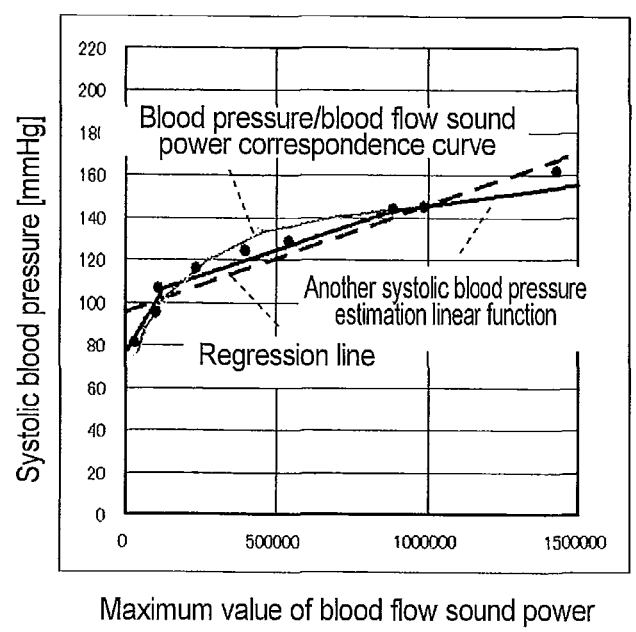
FIG. 42 is a graph showing another systolic blood pressure estimation linear function, regression line, and blood pressure/blood flow sound power correspondence curve of dialysis patient 7.
Figure 43:
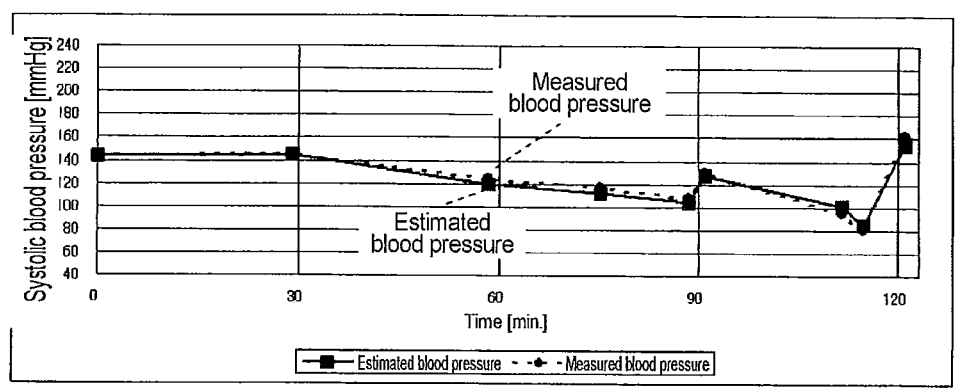
FIG. 43 is a graph showing correspondence between actually measured blood pressure values and estimated blood pressure values of dialysis patient 7.

FIGS. 40 and 42 are graphs of dialysis patients 6 and 7, showing a scatter diagram of the maximum value of blood flow sound power vs. systolic blood pressure, together with a regression line, a blood pressure/blood flow sound power correspondence curve, and the first systolic blood pressure estimation linear functions of Eqs. (4) and (10), while FIGS. 41 and 43 are graphs comparing estimated blood pressure values with measured blood pressure values. As can be seen from FIGS. 40 and 42, the another systolic blood pressure estimation linear function of Eq. (10) nearly approximates a neighborhood of the lower end of the blood pressure/blood flow sound power correspondence curve. Also, it can be seen from FIGS. 41 and 43 that blood pressure is estimated accurately in the dialytic hypotension interval as well.

Although seven points SP0, SP1, SP2, SP3, SP4, SP5, and SP6 are used as representative points on the blood pressure/blood flow sound power correspondence curve in the description of the blood pressure estimation linear function in FIG. 19, the number of representative points is not limited to seven. For example, when N points obtained by dividing the standardized time 0.0 to 1.0 into N−1 parts are used, a systolic blood pressure estimation linear function can be determined from Eqs. (4), (7), and (10) by designating (s6,p6) as (sN,pN) and selecting points corresponding to the intermediate points (s1,p1), ..., (s5,p5).

To correct deviations in correspondence between estimated blood pressure and blood flow sound power caused when a standard pulse curve of unspecified subjects is used, equations may be set up as follows by introducing correction coefficients $\alpha 1$, $\alpha 2$, and $\alpha 3$.

$a1'=\alpha 1 \times a1$  Eq. (11)

$a2'=\alpha 2 \times a2$  Eq. (12)

$a3'=\alpha 3 \times a3$  Eq. (13)

Then, blood pressure may be estimated using a1', a2', and a3'. In the blood pressure estimation linear function created first, $\alpha 1 = \alpha 2 = \alpha 3 = 1$. Subsequently, the systolic blood pressure estimation linear function may be corrected and the value of $\alpha$ may be adjusted again during dialysis by taking a reference blood flow sound measurement and reference blood pressure measurement. The correction may be repeated during the dialysis.

In Eqs. (4) and (7) described above, the Y intercept of the systolic blood pressure estimation linear function is set to pass through the average maximum value of blood flow sound power and the reference systolic blood pressure value around the time of reference blood pressure measurement. However, if the pulse pressure fluctuates abruptly due to arrhythmia or the like during blood pressure measurement for reference and the blood pressure takes an abnormal value, unless the blood flow sound power takes maximum and minimum values corresponding to the abnormal blood pressure value, the blood flow sound power may be plotted by deviating greatly from the regression line, and consequently, the systolic blood pressure estimation linear function passing through the point may not be able to approximate the regression line accurately. To deal with this, a possible method involves installing an acoustic wave sensor or vibration sensor on a cuff, picking up Korotkoff sounds during deflation of the cuff, and identifying and using the maximum value of blood flow sound power at the time of measurement of the reference systolic blood pressure.

Figure 44:
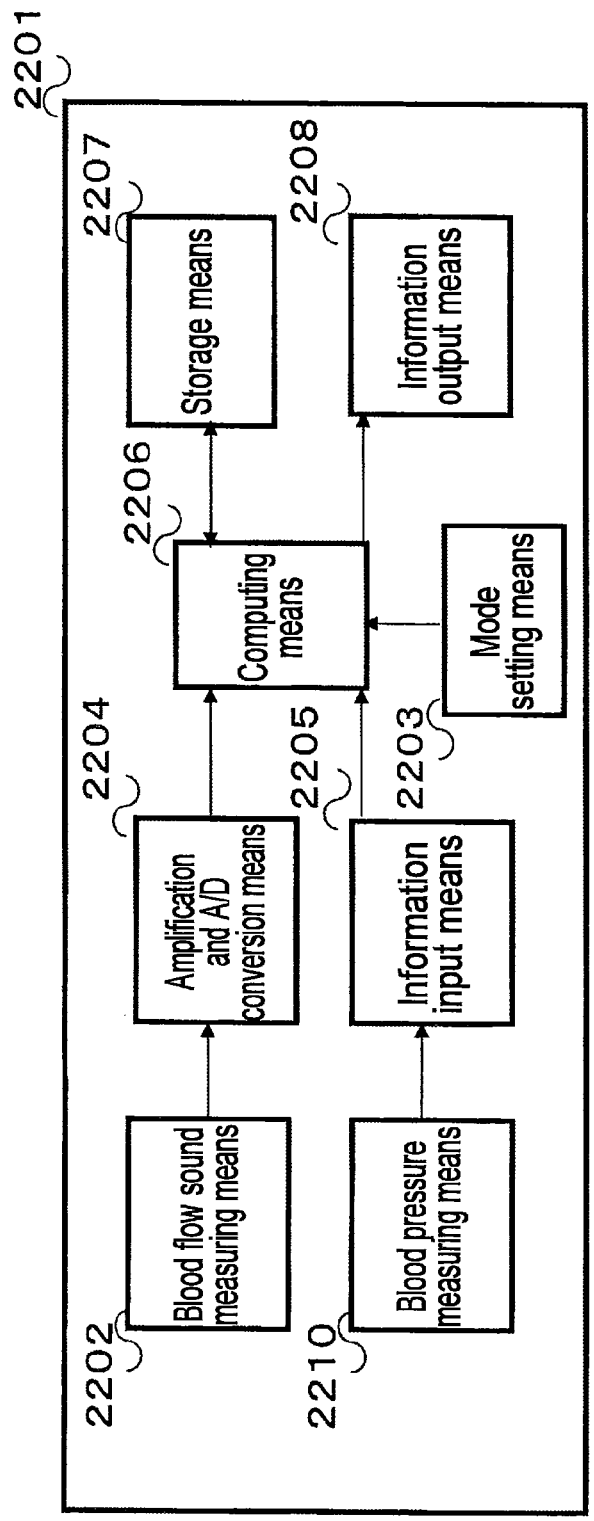
FIG. 44 is a block diagram of an apparatus.

A configuration example of the blood pressure estimation apparatus according to the present invention is shown in FIG. 44.

Reference numeral 2201 denotes the entire blood pressure estimation apparatus, which includes blood flow sound measuring means 2202 such as a stethoscope, computing means 2206 including a CPU and programs, storage means 2207 such as a memory, information input means 2205 such as a touch panel, mode setting means 2203 incorporated by a program or the like, information output means 2208 such as a display, amplification and A/D conversion means 2204, and blood pressure measuring means 2210.

The information input means 2205 inputs the reference diastolic blood pressure value and reference systolic blood pressure value measured by the blood pressure measuring means 2210, measurement timing thereof, and a standard pulse curve. The reference blood pressure values and measurement timing thereof may be captured into the information input means 2205 from the blood pressure measuring means 2210 automatically.

The storage means 2207 includes blood pressure value storing means which stores the reference diastolic blood pressure values and reference systolic blood pressure values inputted from the information input means 2205 as well as standard pulse curve storing means which stores a standard pulse curve.

The mode setting means 2203 is used to set one of a standardization mode shown in FIG. 1 and estimation mode shown in FIG. 2. With the mode setting means 2203 set to the standardization mode, the blood pressure estimation apparatus 2201 performs the processes described below.

The computing means 2206 includes first to sixth computing means and blood flow sound power waveform calculation means. The first computing means determines a correspondence curve which represents a relationship between blood flow sound power and estimated blood pressure from relationships among the blood flow sound power waveform, reference systolic blood pressure, reference diastolic blood pressure, and standard pulse curve in the standardization mode. The second computing means continuously estimates blood pressure from the blood flow sound power measured continuously, using the correspondence curve in the estimation mode. The first computing means further includes the third to fifth computing means. The third computing means creates a reference blood pressure curve which represents a relationship of blood pressure values to standardized time based on the standard pulse curve by bringing the reference systolic blood pressure value and the reference diastolic blood pressure value measured by the blood pressure measuring means 2210 into correspondence with a minimum value and a maximum value of standardized pulse pressure values of the standard pulse curve, respectively.

The fourth computing means standardizes a time axis in a rising phase of the blood flow sound power waveform at the time corresponding to the time of measurement of the reference diastolic blood pressure value and the reference systolic blood pressure value and creates a reference blood flow sound power curve which represents a relationship of the blood flow sound power to the standardized time. The fifth computing means creates the correspondence curve which represents a relationship between the blood flow sound power and the estimated blood pressure in a period of common standardized time based on a relationship between the reference blood pressure curve and the reference blood flow sound power curve in the period of common standardized time.

The first computing means further includes the sixth computing means. The sixth computing means calculates a systolic blood pressure estimation linear function which approximates the correspondence curve by passing through a point on the correspondence curve corresponding to an end point of standardized time. The second computing means inputs a maximum value of the blood flow sound power measured by the blood flow sound power measuring means into the systolic blood pressure estimation linear function and thereby determines estimated systolic blood pressure.

The sixth computing means calculates a first systolic blood pressure estimation linear function for the subject and a second systolic blood pressure estimation linear function for the subject, where according to the first systolic blood pressure estimation linear function for the subject, the maximum value of the blood flow sound power during blood pressure estimation falls below the maximum value of the blood flow sound power at the time of measurement of the reference diastolic blood pressure value and the reference systolic blood pressure value and according to the second systolic blood pressure estimation linear function for the subject, the maximum value of the blood flow sound power during blood pressure estimation rises above the maximum value of the blood flow sound power at the time of measurement of the reference diastolic blood pressure value and the reference systolic blood pressure value. The second computing means determines the estimated systolic blood pressure using the first systolic blood pressure estimation linear function or the second systolic blood pressure estimation linear function depending on variations in the maximum value of the blood flow sound power of the subject during blood pressure estimation.

In the standardization mode, the standard pulse curve is converted into a reference blood pressure curve by the third computing means of the computing means 2206. The blood flow sound measuring means (blood flow sound power measuring means) 2202 includes a sensor for use to pick up blood flow sounds and is capable of continuously measuring blood flow sounds at a shunt site. An analog signal of the blood flow sound sensor picked up by the blood flow sound measuring means 2202 is amplified and converted into a digital signal by the amplification and A/D conversion means 2204 and guided to the computing means 2206. Using the blood flow sound power waveform calculation means, the computing means 2206 creates a blood flow sound power waveform from the digital signal of the blood flow sounds and calculates a maximum value of the blood flow sound power from the blood flow sound power waveform. Also, using the fourth computing means, the computing means 2206 standardizes a time axis in a rising phase of the blood flow sound power waveform at the time corresponding to the time of measurement of the reference diastolic blood pressure value and the reference systolic blood pressure value and creates a reference blood flow sound power curve which represents a relationship of the blood flow sound power to the standardized time. The computing means 2206 determines a correspondence curve between estimated blood pressure and blood flow sound power from the reference blood pressure curve and the reference blood flow sound power curve using the fifth computing means. Also, using the sixth computing means, the computing means 2206 calculates a systolic blood pressure estimation linear function which approximates the correspondence curve by passing through a point on the correspondence curve corresponding to an end point of standardized time. The systolic blood pressure estimation linear function is stored by the storage means 2207. In the estimation mode, the second computing means inputs a maximum value of the blood flow sound power measured by the blood flow sound measuring means 2202 into the systolic blood pressure estimation linear function obtained by the sixth computing means and thereby determines estimated systolic blood pressure.

Also, in the standardization mode, the sixth computing means calculates a first systolic blood pressure estimation linear function for the subject and a second systolic blood pressure estimation linear function for the subject, where according to the first systolic blood pressure estimation linear function the maximum value of the blood flow sound power falls below the reference blood flow sound power value during blood pressure estimation and according to the second systolic blood pressure estimation linear function, the maximum value of the blood flow sound power rises above the reference blood flow sound power value during blood pressure estimation. In the estimation mode, the second computing means determines the estimated systolic blood pressure using the first systolic blood pressure estimation linear function or the second systolic blood pressure estimation linear function depending on variations in the maximum value of the blood flow sound power of the subject during blood pressure estimation.

Also, the sixth computing means calculates another systolic blood pressure estimation linear function for the subject according to which the maximum value of the blood flow sound power falls to or below a predetermined threshold during the blood pressure estimation, and the second computing means determines the estimated systolic blood pressure using the another systolic blood pressure estimation linear function instead of the first systolic blood pressure estimation linear function if the maximum value of the blood flow sound power of the subject during the blood pressure estimation falls to or below the threshold.

With the mode setting means 2203 set to the estimation mode, the blood pressure estimation apparatus 2201 performs the processes described below.

Blood flow sounds at the shunt site of the dialysis patient are measured by the blood flow sound measuring means 2202. An analog signal of the blood flow sounds is amplified and converted into a digital signal by the amplification and A/D conversion means 2204. Then, a maximum value of blood flow sound power is determined by the computing means 2206. Furthermore, the second computing means of the computing means 2206 inputs the maximum value of blood flow sound power into the systolic blood pressure estimation linear function obtained by the sixth computing means and stored by the storage means 2207 and thereby determines estimated systolic blood pressure. Alternatively, the estimated systolic blood pressure may be outputted by the information output means 2208.

Figure 45:
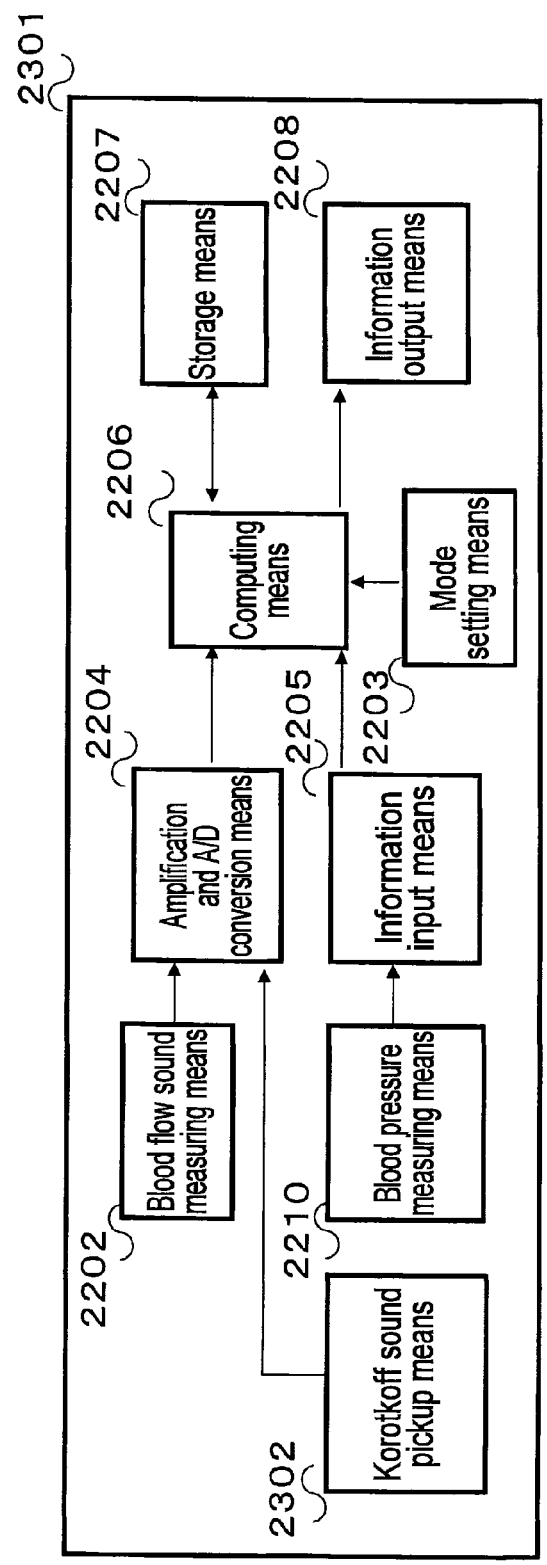
FIG. 45 is a block diagram of an apparatus which uses Korotkoff sounds.

FIG. 45 shows a configuration example of a blood pressure estimation apparatus which picks up Korotkoff sounds during deflation of a cuff, identifies the maximum value of blood flow sound power at the time of measurement of reference systolic blood pressure and reference diastolic blood pressure, and thereby estimates blood pressure.

A difference from the blood pressure estimation apparatus in FIG. 44 is that the blood pressure estimation apparatus in FIG. 45 has Korotkoff sound pickup means 2302, which can pick up Korotkoff sounds during deflation of a cuff using an acoustic wave sensor or vibration sensor installed on the cuff and identify the maximum value of blood flow sound power at the time of measurement of the reference systolic blood pressure and reference diastolic blood pressure.

INDUSTRIAL APPLICABILITY

The present invention provides a non-invasive blood pressure estimation apparatus which measures blood flow sounds at a shunt site of a dialysis patient and thereby estimate systolic blood pressure. Sudden blood pressure changes which could occur during surgery or dialysis can be predicted in advance based on fluctuations in the estimated systolic blood pressure. If frequency of standardization which relates blood pressure and blood flow sound to each other is increased, the apparatus can obtain blood pressure values closer to those measured by an oscillometric method or the like and monitor day-to-day variations of blood pressure, and thus can be used suitably for daily health care.

REFERENCE SIGNS LIST 2201 blood pressure estimation apparatus
2202 blood flow sound measuring means
2206 computing means
2207 storage means

The invention claimed is:

1. A blood pressure estimation apparatus which estimates blood pressure of a subject using a standardization mode and an estimation mode, comprising:
   blood flow sound power waveform calculation means for determining a blood flow sound power waveform from blood flow sound of the subject in the standardization mode;
   blood pressure measuring means for measuring reference systolic blood pressure and reference diastolic blood pressure of the subject in the standardization mode;
   standard pulse curve storing means for storing a standard pulse curve whose time axis and pulse pressure axis have been standardized such that times and pulse pressures at a start point and an end point of a rising phase of a pulse wave measured in advance will be constant, in the standardization mode;
   first computing means for determining a correspondence curve which represents a relationship between blood flow sound power and estimated blood pressure from relationships among the blood flow sound power waveform, the reference systolic blood pressure, the reference diastolic blood pressure, and the standard pulse curve, in the standardization mode;
   blood flow sound power measuring means for continuously measuring the blood flow sound of the subject and the blood flow sound power in the estimation mode; and
   second computing means for continuously estimating blood pressure from the blood flow sound power measured continuously, using the correspondence curve in the estimation mode.

2. The blood pressure estimation apparatus according to claim 1, wherein the first computing means comprises:
   third computing means for creating a reference blood pressure curve which represents a relationship of blood pressure values to standardized time based on the standard pulse curve by bringing the reference diastolic blood pressure value and the reference systolic blood pressure value measured by the blood pressure measuring means into correspondence with a minimum value and a maximum value of standardized pulse pressure values of the standard pulse curve, respectively;
   fourth computing means for standardizing a time axis in a rising phase of the blood flow sound power waveform at the time corresponding to the time of measurement of the reference diastolic blood pressure value and the reference systolic blood pressure value and creating a reference blood flow sound power curve which represents a relationship of the blood flow sound power to the standardized time; and
   fifth computing means for creating the correspondence curve which represents a relationship between the blood flow sound power and the estimated blood pressure in a period of common standardized time based on a relationship between the reference blood pressure curve and the reference blood flow sound power curve in the period of common standardized time.

3. The blood pressure estimation apparatus according to claim 2, wherein
   the first computing means comprises sixth computing means for calculating a systolic blood pressure estimation linear function which approximates the correspondence curve by passing through a point on the correspondence curve corresponding to an end point of the standardized time; and
   the second computing means inputs a maximum value of the blood flow sound power measured by the blood flow sound power measuring means into the systolic blood pressure estimation linear function and thereby determines estimated systolic blood pressure.

4. The blood pressure estimation apparatus according to claim 3, wherein
   the sixth computing means calculates a first systolic blood pressure estimation linear function for the subject and a second systolic blood pressure estimation linear function for the subject, where
      according to the first systolic blood pressure estimation linear function for the subject, the maximum value of the blood flow sound power during blood pressure estimation falls below the maximum value of the blood flow sound power at the time of measurement of the reference diastolic blood pressure value and the reference systolic blood pressure value and
      according to the second systolic blood pressure estimation linear function for the subject, the maximum value of the blood flow sound power during blood pressure estimation rises above the maximum value of the blood flow sound power at the time of measurement of the reference diastolic blood pressure value and the reference systolic blood pressure value; and
   the second computing means determines the estimated systolic blood pressure using the first systolic blood pressure estimation linear function or the second systolic blood pressure estimation linear function depending on variations in the maximum value of the blood flow sound power of the subject during blood pressure estimation.

5. The blood pressure estimation apparatus according to claim 4, wherein
   the sixth computing means calculates another systolic blood pressure estimation linear function for the subject according to which the maximum value of the blood flow sound power falls to or below a predetermined threshold during the blood pressure estimation; and
   the second computing means determines the estimated systolic blood pressure using the another systolic blood pressure estimation linear function instead of the first systolic blood pressure estimation linear function if the maximum value of the blood flow sound power of the subject during the blood pressure estimation falls to or below the threshold.

6. The blood pressure estimation apparatus according to claim 5, wherein

When the maximum value of the blood flow sound power is equal to the threshold, the another systolic blood pressure estimation linear function has a point of intersection with the first systolic blood pressure estimation linear function and approximates the correspondence curve in a range in which the maximum value of the blood flow sound power is not above the threshold.

7. The blood pressure estimation apparatus according to any one of claims 4 to 6, wherein the first systolic blood pressure estimation linear function is defined by a line which has a slope joining a point existing between 5/12 and 7/12 (both inclusive) of the standardized time and a point existing between 9/12 and 11/12 (both inclusive) of the standardized time when a start point and the end point of the standardized time on the correspondence curve obtained by the fifth computing means are taken as 0 and 1, respectively; and the second systolic blood pressure estimation linear function is defined by a line which has a slope joining that point on the correspondence curve which corresponds to the end point of the standardized time and a point existing between 9/12 and 11/12 (both inclusive) of the standardized time when the start point and the end point of the standardized time on the correspondence curve obtained by the fifth computing means are taken as 0 and 1, respectively.

8. The blood pressure estimation apparatus according to any one of claims 3 to 6, wherein during blood pressure estimation performed by the first computing means, a computational operation for finding the systolic blood pressure estimation linear function is performed a plurality of times to correct the systolic blood pressure estimation linear function.

9. The blood pressure estimation apparatus according to any one of claims 1 to 6, further comprising:

mode setting means for setting one of the standardization mode and the estimation mode;

information input means for inputting data of at least the reference diastolic blood pressure value, the reference systolic blood pressure value, and the standard pulse curve;

information output means for outputting at least estimated blood pressure values; and blood pressure value storing means for storing the reference diastolic blood pressure value and the reference systolic blood pressure value.

10. The blood pressure estimation apparatus according to any one of claims 1 to 6, wherein the pulse wave used to create the standard pulse curve is an average of a plurality of pulse waves obtained from a plurality of unspecified subjects.

11. The blood pressure estimation apparatus according to any one of claims 1 to 6, wherein the pulse wave used to create the standard pulse curve is a pulse wave of the subject whose blood pressure is estimated.

12. A blood pressure estimation method for estimating blood pressure of a subject, comprising a standardization mode and an estimation mode, wherein the standardization mode comprises:

a first step of measuring blood flow sound of the subject and determining a blood flow sound power waveform from the measured blood flow sound, a second step of measuring reference systolic blood pressure and reference diastolic blood pressure of the subject, a third step of preparing, using a processor, a standard pulse curve whose time axis and pulse pressure axis have been standardized such that times and pulse pressures at a start point and an end point of a rising phase of a pulse wave measured in advance will be constant, and a fourth step of determining, using the processor, a correspondence curve which represents a relationship between blood flow sound power and estimated blood pressure from relationships among the blood flow sound power waveform, the reference systolic blood pressure, the reference diastolic blood pressure, and the standard pulse curve in the standardization mode; and the estimation mode comprises:

a fifth step of continuously measuring the blood flow sound of the subject and the blood flow sound power, and a sixth step of continuously estimating, using the processor, blood pressure from the blood flow sound power measured continuously, using the correspondence curve in the estimation mode.

13. The blood pressure estimation method according to claim 12, wherein the fourth step comprises:

a step of creating a reference blood pressure curve which represents a relationship of blood pressure values to standardized time based on the standard pulse curve by bringing the reference diastolic blood pressure value and the reference systolic blood pressure value into correspondence with a minimum value and a maximum value of standardized pulse pressure values of the standard pulse curve, respectively;

a step of standardizing a time axis in a rising phase of the blood flow sound power waveform at the time corresponding to the time of measurement of the reference diastolic blood pressure value and the reference systolic blood pressure value and creating a reference blood flow sound power curve which represents a relationship of the blood flow sound power to the standardized time; and a step of creating the correspondence curve which represents a relationship between the blood flow sound power and the estimated blood pressure in a period of common standardized time based on a relationship between the reference blood pressure curve and the reference blood flow sound power curve in the period of common standardized time.

14. The blood pressure estimation method according to claim 13, wherein the fourth step calculates a systolic blood pressure estimation linear function which approximates the correspondence curve by passing through a point on the correspondence curve corresponding to an end point of the standardized time; and the sixth step inputs a maximum value of the blood flow sound power measured by the fifth step into the systolic blood pressure estimation linear function and thereby determines estimated systolic blood pressure.

15. The blood pressure estimation method according to claim 14, wherein the fourth step calculates a first systolic blood pressure estimation linear function for the subject and a second systolic blood pressure estimation linear function for the subject, where according to the first systolic blood pressure estimation linear function for the subject, the maximum value of the blood flow sound power during blood pressure estimation falls below the maximum value of the blood flow sound power at the time of measurement of the reference diastolic blood pressure value and the reference systolic blood pressure value and according to the second systolic blood pressure estimation linear function for the subject, the maximum value of the blood flow sound power during blood pressure estimation rises above the maximum value of the blood flow sound power at the time of measurement of the reference diastolic blood pressure value and the reference systolic blood pressure value; and the sixth step determines the estimated systolic blood pressure using the first systolic blood pressure estimation linear function or the second systolic blood pressure estimation linear function depending on variations in the maximum value of the blood flow sound power of the subject during blood pressure estimation.

16. The blood pressure estimation method according to claim 15, wherein the fourth step calculates another systolic blood pressure estimation linear function for the subject according to which the maximum value of the blood flow sound power falls to or below a predetermined threshold during the blood pressure estimation; and the sixth step determines the estimated systolic blood pressure using the another systolic blood pressure estimation linear function instead of the first systolic blood pressure estimation linear function if the maximum value of the blood flow sound power of the subject during the blood pressure estimation falls to or below the threshold.

* * * * *